(12) United States Patent
Jung et al.

(10) Patent No.: US 10,646,602 B2
(45) Date of Patent: May 12, 2020

(54) METHODS AND SYSTEMS FOR STERILIZATION

(75) Inventors: Edward K. Y. Jung, Bellevue, WA (US); Royce A. Levien, Lexington, MA (US); Robert W. Lord, Seattle, WA (US); Mark A. Malamud, Seattle, WA (US); John D. Rinaldo, Jr., Bellevue, WA (US); Lowell L. Wood, Jr., Bellevue, WA (US)

(73) Assignee: Deep Science, LLC, Bellevue, WA (US)

( * ) Notice: Subject to any disclaimer, the term of this patent is extended or adjusted under 35 U.S.C. 154(b) by 30 days.

(21) Appl. No.: 11/593,193

(22) Filed: Nov. 3, 2006

(65) Prior Publication Data

US 2007/0231194 A1 Oct. 4, 2007

Related U.S. Application Data

(63) Continuation-in-part of application No. 11/396,256, filed on Mar. 31, 2006, now Pat. No. 8,277,724, and a continuation-in-part of application No. 11/411,207, filed on Apr. 25, 2006, now Pat. No. 7,638,090, and a continuation-in-part of application No. 11/414,743, filed on Apr. 28, 2006, now Pat. No. 8,114,342.

(51) Int. Cl.
*A61L 2/24* (2006.01)
*A61L 2/08* (2006.01)
*A61L 2/10* (2006.01)

(52) U.S. Cl.
CPC .............. *A61L 2/081* (2013.01); *A61L 2/082* (2013.01); *A61L 2/084* (2013.01); *A61L 2/087* (2013.01); *A61L 2/10* (2013.01); *A61L 2/24* (2013.01); *A61L 2202/24* (2013.01)

(58) Field of Classification Search
CPC ............................ A61L 2/0029; A61L 2/0047
See application file for complete search history.

(56) References Cited

U.S. PATENT DOCUMENTS

| | | |
|---|---|---|
| 2,216,333 A | 10/1940 | White et al. |
| 2,689,837 A | 9/1954 | Darby et al. |
| 2,873,263 A | 2/1959 | Lal |
| 2,875,097 A | 2/1959 | Pritchard |
| 2,986,448 A | 5/1961 | Gates et al. |
| 3,325,436 A | 6/1967 | Prindle et al. |
| 3,376,110 A | 4/1968 | Shiraeff |
| 3,376,384 A | 4/1968 | Achramowicz |
| 3,480,557 A | 11/1969 | Shiraeff |
| 3,485,787 A | 12/1969 | Haefele et al. |
| 3,827,999 A | 8/1974 | Crossland |

(Continued)

FOREIGN PATENT DOCUMENTS

| | | |
|---|---|---|
| CN | 1638632 A | 7/2005 |
| EP | 0693289 A2 | 1/1996 |

(Continued)

OTHER PUBLICATIONS

U.S. Appl. No. 11/891,357, Jung et al.

(Continued)

*Primary Examiner* — Regina M Yoo

(57) ABSTRACT

The present disclosure relates to sterilization methods and systems that may be used within numerous contexts, such as health-care and manufacturing facilities.

20 Claims, 15 Drawing Sheets

(56) References Cited

U.S. PATENT DOCUMENTS

| | | |
|---|---|---|
| 3,870,783 A | 3/1975 | Hall et al. |
| 3,953,566 A | 4/1976 | Gore |
| 3,966,902 A | 6/1976 | Chromecek |
| 3,967,478 A | 7/1976 | Guinn |
| 4,042,765 A | 8/1977 | Floyd et al. |
| 4,073,764 A | 2/1978 | Hemmerich et al. |
| 4,087,925 A | 5/1978 | Bienek |
| 4,151,419 A | 4/1979 | Morris et al. |
| 4,169,123 A | 9/1979 | Moore et al. |
| 4,169,124 A | 9/1979 | Forstrom et al. |
| 4,176,240 A | 11/1979 | Sabia |
| 4,187,390 A | 2/1980 | Gore |
| 4,194,041 A | 3/1980 | Gore et al. |
| 4,197,375 A | 4/1980 | Fox |
| 4,208,324 A | 6/1980 | Ramanathan |
| 4,312,907 A | 1/1982 | Hiraoka et al. |
| 4,325,870 A | 4/1982 | Bühler et al. |
| 4,369,284 A | 1/1983 | Chen |
| 4,381,380 A | 4/1983 | LeVeen et al. |
| 4,403,826 A | 9/1983 | Presby |
| 4,443,511 A | 4/1984 | Worden et al. |
| 4,476,255 A | 10/1984 | Bailey et al. |
| 4,499,154 A | 2/1985 | James et al. |
| 4,500,455 A | 2/1985 | Niwa et al. |
| 4,556,464 A | 12/1985 | St. Clair |
| 4,612,444 A | 9/1986 | Ragusa |
| 4,618,213 A | 10/1986 | Chen |
| 4,629,896 A | 12/1986 | Bridgen |
| 4,642,165 A | 2/1987 | Bier |
| 4,643,876 A | 2/1987 | Jacobs et al. |
| 4,688,585 A | 8/1987 | Vetter |
| 4,688,858 A | 8/1987 | Fennel et al. |
| 4,692,369 A | 9/1987 | Nomi |
| 4,716,183 A | 12/1987 | Gamarra et al. |
| 4,731,541 A | 3/1988 | Shoemaker |
| 4,744,951 A | 5/1988 | Cummings et al. |
| 4,771,482 A | 9/1988 | Shlenker |
| 4,774,324 A | 9/1988 | Loeffler et al. |
| 4,855,412 A | 8/1989 | Dehnert et al. |
| 4,855,413 A | 8/1989 | Dehnert et al. |
| 4,907,316 A | 3/1990 | Kurz |
| 4,925,732 A | 5/1990 | Driskill et al. |
| 4,935,260 A | 6/1990 | Shlenker |
| 4,935,635 A | 6/1990 | O'Harra |
| 4,942,270 A | 7/1990 | Gamarra |
| 4,943,414 A | 7/1990 | Jacobs et al. |
| 5,008,093 A | 4/1991 | Merianos |
| 5,008,106 A | 4/1991 | Merianos et al. |
| 5,030,380 A | 7/1991 | Moschner et al. |
| 5,061,106 A | 10/1991 | Kent |
| 5,069,227 A | 12/1991 | Maronian |
| 5,074,322 A | 12/1991 | Jaw |
| 5,077,047 A | 12/1991 | Biss et al. |
| 5,102,711 A | 4/1992 | Keller et al. |
| 5,113,874 A | 5/1992 | Maronian |
| 5,138,719 A | 8/1992 | Orlianges et al. |
| 5,142,010 A | 8/1992 | Olstein |
| 5,240,675 A * | 8/1993 | Wilk et al. ............ 422/22 |
| 5,269,981 A | 12/1993 | Jameson et al. |
| 5,315,289 A | 5/1994 | Fuller et al. |
| 5,326,841 A | 7/1994 | Fellman |
| 5,357,636 A | 10/1994 | Dresdner, Jr. et al. |
| 5,360,892 A | 11/1994 | Bonsignore et al. |
| 5,403,363 A | 4/1995 | Loeffler et al. |
| 5,428,123 A | 6/1995 | Ward et al. |
| 5,459,879 A | 10/1995 | Fuchs |
| 5,480,915 A | 1/1996 | Burns |
| 5,498,394 A | 3/1996 | Matschke |
| 5,501,669 A | 3/1996 | Conway et al. |
| 5,547,635 A | 8/1996 | Duthie, Jr. |
| 5,549,924 A | 8/1996 | Shlenker et al. |
| 5,557,444 A | 9/1996 | Melville et al. |
| 5,563,238 A | 10/1996 | Bonsignore et al. |
| 5,614,151 A | 3/1997 | LeVay et al. |
| 5,641,566 A | 6/1997 | Kranzler et al. |
| H1670 H | 7/1997 | Aziz et al. |
| 5,644,798 A | 7/1997 | Shah |
| 5,648,003 A | 7/1997 | Liang et al. |
| 5,667,753 A | 9/1997 | Jacobs et al. |
| 5,688,475 A | 11/1997 | Duthie, Jr. |
| 5,731,053 A | 3/1998 | Kuhn et al. |
| 5,733,270 A | 3/1998 | Ling et al. |
| 5,779,795 A | 7/1998 | Bucher et al. |
| 5,782,382 A | 7/1998 | Van Marcke |
| 5,783,290 A | 7/1998 | Isaac et al. |
| 5,786,598 A | 7/1998 | Clark et al. |
| 5,788,925 A | 8/1998 | Pai et al. |
| 5,788,940 A | 8/1998 | Cicha et al. |
| 5,798,165 A | 8/1998 | Mizoguchi et al. |
| 5,808,553 A | 9/1998 | Cunningham |
| 5,851,551 A | 12/1998 | Tseng et al. |
| 5,891,399 A | 4/1999 | Owesen |
| 5,901,564 A | 5/1999 | Comeau, II |
| 5,920,075 A | 7/1999 | Whitehead |
| 5,945,068 A | 8/1999 | Ferone |
| 5,945,910 A | 8/1999 | Gorra |
| 5,948,707 A | 9/1999 | Crawley et al. |
| 5,959,423 A | 9/1999 | Nakanishi et al. |
| 5,965,276 A | 10/1999 | Shlenker et al. |
| 6,010,727 A | 1/2000 | Rosenthal |
| 6,038,331 A | 3/2000 | Johnson |
| 6,132,784 A | 10/2000 | Brandt et al. |
| 6,177,677 B1 | 1/2001 | Alboresi et al. |
| 6,192,887 B1 | 2/2001 | Howett et al. |
| 6,193,931 B1 | 2/2001 | Lin et al. |
| 6,223,137 B1 | 4/2001 | McCay et al. |
| 6,252,128 B1 | 6/2001 | Obata |
| 6,254,065 B1 | 7/2001 | Ehrensperger et al. |
| 6,254,625 B1 | 7/2001 | Rosenthal et al. |
| 6,311,974 B1 | 11/2001 | Koga |
| 6,326,654 B1 | 12/2001 | Ruden et al. |
| 6,335,529 B1 | 1/2002 | Sekii et al. |
| 6,343,425 B1 * | 2/2002 | Sias et al. ............ 34/389 |
| 6,370,694 B1 | 4/2002 | Michelson |
| 6,426,701 B1 | 7/2002 | Levy et al. |
| 6,429,438 B1 | 8/2002 | Smestad |
| 6,459,955 B1 | 10/2002 | Bartsch et al. |
| 6,485,979 B1 | 11/2002 | Kippenhan et al. |
| 6,490,351 B1 | 12/2002 | Roberts |
| 6,521,552 B1 | 2/2003 | Honna et al. |
| 6,524,698 B1 | 2/2003 | Schmoock |
| 6,530,498 B1 | 3/2003 | Ovadia |
| 6,560,782 B2 | 5/2003 | Hourihan et al. |
| 6,573,836 B1 | 6/2003 | Gitis et al. |
| 6,577,240 B2 * | 6/2003 | Armstrong ............ 340/573.1 |
| 6,610,254 B1 | 8/2003 | Furner et al. |
| 6,656,424 B1 | 12/2003 | Deal |
| 6,663,805 B1 | 12/2003 | Ekiner et al. |
| 6,676,871 B1 | 1/2004 | Benassi et al. |
| 6,706,243 B1 | 3/2004 | Sias et al. |
| 6,716,352 B1 | 4/2004 | Livingston |
| 6,727,818 B1 * | 4/2004 | Wildman et al. ....... 340/573.1 |
| 6,733,495 B1 | 5/2004 | Bek et al. |
| 6,755,536 B2 | 6/2004 | Tegreene et al. |
| 6,765,029 B2 | 7/2004 | Sasabe et al. |
| 6,806,361 B1 | 10/2004 | Kajisa et al. |
| 6,872,366 B2 | 3/2005 | Thomas et al. |
| 6,882,278 B2 | 4/2005 | Winings et al. |
| 6,901,712 B2 | 6/2005 | Lionel |
| 6,911,177 B2 | 6/2005 | Deal |
| 6,913,758 B2 | 7/2005 | Hourihan et al. |
| 6,925,679 B2 | 8/2005 | Wallach et al. |
| 6,937,221 B2 | 8/2005 | Lippert et al. |
| 6,949,222 B1 | 9/2005 | Möller et al. |
| 6,961,541 B2 | 11/2005 | Overy et al. |
| 6,963,289 B2 | 11/2005 | Aljadeff et al. |
| 6,968,194 B2 | 11/2005 | Aljadeff et al. |
| 6,991,761 B2 | 1/2006 | Hehenberger et al. |
| 7,009,185 B2 | 3/2006 | Chi et al. |
| 7,015,816 B2 | 3/2006 | Wildman et al. |
| 7,056,971 B2 | 6/2006 | Varma |
| 7,101,408 B2 | 9/2006 | Himeno et al. |
| 7,104,519 B2 | 9/2006 | O'Maley et al. |
| 7,122,150 B2 | 10/2006 | Gonzalez et al. |

(56) References Cited

U.S. PATENT DOCUMENTS

| | | | |
|---|---|---|---|
| 7,149,531 B2 | 12/2006 | Misikangas | |
| 7,175,807 B1 | 2/2007 | Jones | |
| 7,196,662 B2 | 3/2007 | Misikangas et al. | |
| 7,209,752 B2 | 4/2007 | Myllymäki et al. | |
| 7,228,136 B2 | 6/2007 | Myllymäki et al. | |
| 7,286,057 B2 | 10/2007 | Bolling | |
| 7,295,115 B2 | 11/2007 | Aljadeff et al. | |
| 7,299,059 B2 | 11/2007 | Misikangas et al. | |
| 7,300,770 B2 * | 11/2007 | Martin et al. | 435/31 |
| 7,349,683 B2 | 3/2008 | Misikangas et al. | |
| 7,403,108 B2 | 7/2008 | Aljadeff et al. | |
| 7,408,470 B2 | 8/2008 | Wildman et al. | |
| 7,482,936 B2 | 1/2009 | Bolling | |
| 7,522,049 B2 | 4/2009 | Aljadeff et al. | |
| 7,616,122 B2 | 11/2009 | Bolling | |
| 7,616,124 B2 | 11/2009 | Paessel et al. | |
| 7,682,696 B2 * | 3/2010 | Dean et al. | 428/412 |
| 7,729,707 B2 | 6/2010 | Aljadeff et al. | |
| 7,904,097 B2 | 3/2011 | Misikangas | |
| 7,936,275 B2 | 5/2011 | Bolling | |
| 7,982,619 B2 | 7/2011 | Bolling | |
| 8,020,733 B2 | 9/2011 | Snodgrass | |
| 8,056,768 B2 | 11/2011 | Snodgrass | |
| 8,208,939 B2 | 6/2012 | Aljadeff et al. | |
| 2002/0011934 A1 * | 1/2002 | Cacioli et al. | 340/604 |
| 2002/0085947 A1 | 7/2002 | Deal | |
| 2002/0158814 A1 | 10/2002 | Bright et al. | |
| 2002/0175182 A1 | 11/2002 | Matthews | |
| 2002/0192340 A1 | 12/2002 | Swart et al. | |
| 2003/0030562 A1 | 2/2003 | Lane et al. | |
| 2003/0081293 A1 | 5/2003 | Wood, Jr. et al. | |
| 2003/0093503 A1 | 5/2003 | Yamaki et al. | |
| 2003/0145664 A1 | 8/2003 | Schwarz et al. | |
| 2003/0164285 A1 | 9/2003 | Korenev | |
| 2003/0170901 A1 | 9/2003 | Kippenhan et al. | |
| 2003/0194344 A1 | 10/2003 | Brafford et al. | |
| 2003/0235605 A1 | 12/2003 | Lelah et al. | |
| 2004/0024290 A1 * | 2/2004 | Root et al. | 600/160 |
| 2004/0052679 A1 * | 3/2004 | Root et al. | 422/1 |
| 2004/0056201 A1 | 3/2004 | Fink et al. | |
| 2004/0072577 A1 | 4/2004 | Myllymaki et al. | |
| 2004/0090333 A1 | 5/2004 | Wildman et al. | |
| 2004/0120844 A1 | 6/2004 | Tribelsky et al. | |
| 2004/0139555 A1 | 7/2004 | Conrad et al. | |
| 2004/0176108 A1 | 9/2004 | Misikangas | |
| 2004/0203870 A1 | 10/2004 | Aljadeff et al. | |
| 2004/0211444 A1 | 10/2004 | Taylor et al. | |
| 2004/0244138 A1 | 12/2004 | Taylor et al. | |
| 2005/0013729 A1 | 1/2005 | Brown-Skrobot et al. | |
| 2005/0022844 A1 | 2/2005 | Field et al. | |
| 2005/0069453 A1 | 3/2005 | Forng et al. | |
| 2005/0128139 A1 | 6/2005 | Misikangas et al. | |
| 2005/0131635 A1 | 6/2005 | Myllymaki et al. | |
| 2005/0135965 A1 | 6/2005 | Williams et al. | |
| 2005/0136944 A1 | 6/2005 | Misikangas et al. | |
| 2005/0156711 A1 | 7/2005 | Aljadeff et al. | |
| 2005/0181804 A1 | 8/2005 | Misikangas et al. | |
| 2005/0186108 A1 | 8/2005 | Fields | |
| 2005/0197139 A1 | 9/2005 | Misikangas et al. | |
| 2005/0207381 A1 | 9/2005 | Aljadeff et al. | |
| 2005/0214506 A1 | 9/2005 | Lee et al. | |
| 2005/0236579 A1 | 10/2005 | Jenkins et al. | |
| 2005/0249791 A1 | 11/2005 | Hobbs et al. | |
| 2005/0267233 A1 | 12/2005 | Joshi | |
| 2006/0028373 A1 | 2/2006 | Fullerton et al. | |
| 2006/0071799 A1 * | 4/2006 | Verdiramo | 340/573.5 |
| 2006/0167531 A1 | 7/2006 | Gertner et al. | |
| 2006/0216193 A1 | 9/2006 | Johnson et al. | |
| 2006/0236496 A1 | 10/2006 | Oh et al. | |
| 2006/0259195 A1 | 11/2006 | Eliuk et al. | |
| 2006/0273915 A1 | 12/2006 | Snodgrass | |
| 2007/0008149 A1 | 1/2007 | Bolling | |
| 2007/0046460 A1 | 3/2007 | Aljadeff et al. | |
| 2007/0103296 A1 | 5/2007 | Paessel et al. | |
| 2007/0117568 A1 | 5/2007 | Misikangas et al. | |
| 2007/0149215 A1 | 6/2007 | Misikangas | |
| 2007/0219600 A1 | 9/2007 | Gertner et al. | |
| 2008/0037512 A1 | 2/2008 | Aljadeff et al. | |
| 2008/0184518 A1 | 8/2008 | Taylor et al. | |
| 2008/0186231 A1 | 8/2008 | Aljadeff et al. | |
| 2008/0283786 A1 | 11/2008 | Snodgrass | |
| 2009/0166382 A1 | 7/2009 | Snodgrass | |
| 2009/0266842 A1 | 10/2009 | Snodgrass | |
| 2009/0273465 A1 | 11/2009 | Shamir et al. | |
| 2010/0117823 A1 | 5/2010 | Wholtjen | |
| 2010/0123560 A1 | 5/2010 | Nix et al. | |
| 2010/0262430 A1 | 10/2010 | Gips et al. | |
| 2010/0297602 A1 | 11/2010 | Jones, Jr. | |
| 2010/0308076 A1 | 12/2010 | Snodgrass | |
| 2011/0018769 A1 | 1/2011 | Misikangas et al. | |
| 2011/0050501 A1 | 3/2011 | Aljadeff | |
| 2011/0063106 A1 | 3/2011 | Snodgrass | |
| 2011/0163870 A1 | 7/2011 | Snodgrass | |
| 2011/0195701 A1 | 8/2011 | Cook et al. | |
| 2011/0227740 A1 | 9/2011 | Wohltjen | |
| 2011/0291841 A1 | 12/2011 | Hollock et al. | |

FOREIGN PATENT DOCUMENTS

| | | |
|---|---|---|
| EP | 1 537 796 A2 | 6/2005 |
| EP | 1 609 488 A | 12/2005 |
| EP | 1 609 488 A1 | 12/2005 |
| EP | 2 180 334 A3 | 4/2010 |
| GB | 2291350 A | 1/1996 |
| JP | 01139139 A | 5/1989 |
| JP | 07289616 A | 11/1995 |
| JP | 08071132 A | 3/1996 |
| JP | 08071133 A | 3/1996 |
| JP | 08215110 | 8/1996 |
| JP | 08-266595 | 10/1996 |
| JP | 2000220334 | 8/2000 |
| JP | 2001-25501 | 1/2001 |
| JP | 2002364055 | 12/2002 |
| JP | 2003250865 | 9/2003 |
| JP | 2004317512 A | 11/2004 |
| KR | 10-2004-0031733 | 3/2004 |
| KR | 10-2005-0112195 | 11/2005 |
| WO | WO 95/17634 | 6/1995 |
| WO | WO 01/10476 A1 | 2/2001 |
| WO | WO 01/60419 A1 | 8/2001 |
| WO | WO 03/056951 A2 | 7/2003 |
| WO | WO 2004/032019 A2 | 4/2004 |
| WO | WO 2004/035095 A1 | 4/2004 |
| WO | WO2004/080494 A1 | 9/2004 |
| WO | WO 2005048041 A2 * | 5/2005 |
| WO | WO2005/077076 A2 | 8/2005 |
| WO | WO 2006/007729 A1 | 1/2006 |
| WO | WO 2006/026436 A2 | 3/2006 |
| WO | WO 2010/059678 A2 | 5/2010 |
| WO | WO 2011/033504 A1 | 3/2011 |
| WO | WO 2011/058228 A1 | 5/2011 |

OTHER PUBLICATIONS

PCT International Search Report; International App. No. PCT/US07/23129; dated Apr. 10, 2008; pp. 1-2.

PCT International Search Report; International App. No. PCT/US07/07582; dated Apr. 11, 2008; pp. 1-2.

U.S. Appl. No. 11/584,435, Jung et al.

U.S. Appl. No. 11/584,339, Hyde et al.

U.S. Appl. No. 11/442,699, Jung et al.

U.S. Appl. No. 11/442,688, Jung et al.

Advanced Sterilization Products; "Frequently Asked Questions"; pp. 1-3; located at http://www.sterrad.com/products_&_services/sterrad/sterrad_nx/faqs/index.asp; bearing a date of 2006; Advanced Sterilization Products; printed on Mar. 3, 2006.

Big Sky Laser; "Nd:YAG & Dye Laboratory Lasers from Quantel"; pp. 1-4; located at http://www.bigskylaser.com/lablasers.html#tdl190; printed on Mar. 22, 2006.

Big Sky Laser; "The Brilliant Series of Nd:YAG laser oscillators and accessories"; p. 1; located at http://www.bigskylaser.com/brilliantseries.html; printed on Mar. 22, 2006.

(56) References Cited

OTHER PUBLICATIONS

Creative Concepts; "Creative Oz-Air (i) Pvt. Ltd: Ozone Ambient Air Monitor & Controller, Hands Sterilizer, U.V. Systems, Ozone Test Kits, Ozone aCCESSORIES"; pp. 1-3; Creative Oz-Air (i) Pvt. Ltd.; located at http://www.creativeconceptsozair.com/ozoneambient.html/#handsterilizer; printed on Apr. 25, 2006.
De Kock, Servaas; "Marketplace: Ozone Dry hand Sterilizing Unit"; pp. 1-2; located at http://www.ecademy.com/module.php?mod=list&lid=11053; bearing a date of Dec. 3, 2005; Ecademy; Cape Town, South Africa; printed on Apr. 25, 2006.
Elgan, Mike; "The Raw Feed Archives: Unexpected Convergence: Mouse and Hand Sterilizer"; pp. 1-6; located at http://www.mikeslist.com/2003_09_28_archive.html; bearing a date of Oct. 4, 2003; Mike's List; printed on Apr. 25, 2006.
Enhance-It; "Mobile Room Sterilizers"; p. 1; located at http://www.enhance-it.com/06mobile.htm; bearing a date of 1999-2006; Enhance-It LLC; printed on Mar. 22, 2006.
Enhance-It; "Portable Germicidal Units"; p. 1; located at http://www.enhance-it.com/05portable.htm; bearing a date of 1999-2006; Enhance-It LLC; printed on Mar. 22, 2006.
Enhance-It, "Portable Germicidal Units". p. 1, located at http://www.enhance-it.com/04portable.htm, bearing a date of 1999-2006, Enhance-It LLC; printed on Mar. 22, 2006.
Enhance-It; "Ultraviolet Light"; p. 1-2; located at http://www.enhance-it.com/uaprod.htm; bearing a date of 1999-2006; Enhance-It LLC; printed on Mar. 22, 2006.
GLOBALSPEC; "About UV Light Systems"; pp. 1-3; located at http://light-sources.globalspec.com/LearnMore/Ootics_Optical_Components/Light_Sources/Process_UV_Lamps_Systems; bearing a date of 1999-2006; Globalspec, Inc.; printed on Mar. 22, 2006.
Hilton, Paul; "Nd:YAG laser welding"; TWI World Centre for Materials Joining Technology; pp. 1-2; located at http://www.twi.co.uk/j32k/protected/band_3/kspah003.html; bearing a date of 2001; TWI Ltd; printed on Mar. 22, 2006.
HRS; "Specialty/Hygiene System-Hand Sterilizer" pp. 1-2; located at http://www.hrs.co.kr/english/hrs_specialty_hand.htm; bearing a date of 2004; HRS, Seoul, South Korea; printed on Apr. 25, 2006.
Marhoc; "Marhoc's Automatic Hand Sterilizer U.S. Pat. No. 6,872,366" pp. 1-3; located at http://www.marhoc.com/Marhoc_Hand_Sterilizer.htm; bearing a date of 2005; printed on Apr. 25, 2006.
Medical Device Link; "Equipment News: Packaging and Sterilization Equipment—Machine Designers Address Space, Validation Issues"; Medical Product Manufacturing News; pp. 1-5; located at http://www.devicelink.com/mpmn/archive/01/04/004.html; bearing a date of Apr. 2001; printed on Mar. 22, 2006.
Nehmzow, U.; "Mobile Robotics: A Practical Introduction," $2^{nd}$ Edition, 2003, ISBN No. 1852337265, Springer, London, UK (not provided).
Olgear; "Ozone Dry Hand Sterilising unit"; pp. 1-2; located at http://www.olgear.com/sites/58/images/ozone_hand_steriliser.pdf.
Siegwart, Roland; Nourbakhsh, Illah R.; "Introduction to Autonomous Mobile Robots," 2004, ISBN No. 0-262-19502-X, The MIT Press, Cumberland, RI. (not provided).
Tidybio; "No-touch fully inductive control: Quick-speed and efficient sterilization: No need of water supply and quick-speed air-drying: Easy Operation without waste"; pp. 1-7; located at http://www.tidybio.cn/english/Sterilizer.shtml; bearing a date of 2003-2005; Beijing Tidybio Science & Technology Co., Ltd., printed on Apr. 25, 2006.
Wikipedia; "Nd:YAG laser"; pp. 1-2; located at http://en.wikipedia.org/wiki/Nd-YAG_laser; bearing a date of Feb. 23, 2006; printed on Mar. 22, 2006.
Xenon Corporation; "SteriPulse-XL-Sterilization and Decontamination Systems"; pp. 1-6; located at http://www.xenoncorp.com/sterilization.html; printed on Mar. 23, 2006.
Xie, Ming; "Fundamentals of Robotics: Linking Perception to Action," 2003, ISBN No. 9812383131, World Scientific Publishing Co. Pte. Ltd., River Edge, NJ (not provided).
U.S. Appl. No. 11/592,010, Ishikawa et al.
"CDC Urges Hospitals to Tackle Drug-Resistant Infections"; The Wall Street Journal; bearing a date of Oct. 19, 2006; pp. 1-2; printed on Oct. 31, 2006.
Smith, Ann; Heckelman, Patricia E.; O'Neil, Maryadele J. (Ed); Budavari, Susan (Ed); The Merck Index: An Encyclopedia of Chemicals, Drugs and Biologicals; bearing a date of Oct. 2001; 2564 pages; $13^{th}$ Edition; ISBN No. 0911910131; John Wiley and Sons and Merck & Co. Inc.; Whitehouse Station, NJ (not provided).
Smith, Michael; "ICAAC: Rhinovirus on Hands Blocked by Solution for Hours"; MedPage Today; Bearing dates of Oct. 2, 2006 and 2004-2006; pp. 1-2; San Francisco; MedPage Today, LLC; printed on Oct. 19, 2006.
PCT International Search Report; International App. No. PCT/US 07/07846, dated Nov. 18, 2008, pp. 1-2.
PCT International Search Report; International App. No. PCT/US07/07673, dated Oct. 10, 2008, pp. 1-2.
PCT International Search Report; International App. No. PCT/US07/07845, dated Sep. 18, 2008, pp. 1-2.
U.S. Appl. No. 12/384,168, Jung et al.
U.S. Appl. No. 12/384,166, Jung et al.
U.S. Appl. No. 60/605,066, filed Aug. 27, 2004, Taylor, Charles E.
European Search Report; European App. No. EP 07 75 4150; dated Sep. 14, 2009; pp. 1-6.
U.S. Appl. No. 12/587,143, Jung et al.
U.S. Appl. No. 12/587,142, Jung et al.
U.S. Appl. No. 12/587,104, Hyde et al.
Supplementary European Search Report; European App. No. 07774171.8; date Sep. 14, 2009; 6 Total Pages.
Supplementary European Search Report; European App. No. 07754226.4; dated Sep. 14, 2009; 7 Total Pages.
Supplementary European Search Report; European App. No. 07754375.9; dated Sep. 14, 2009; 6 Total Pages.
Supplementary European Search Report; European App. No. 07754150.6; dated Sep. 14, 2009; 6 Total Pages.
U.S. Appl. No. 12/800,814, Hyde et al.
State Intellectual Property Office of P.R.C.; Application No. 200780040949.2; dated Jul. 16, 2010; pp. 1-7.
UK Intellectual Property Office Examination Report Under Section 18(3); App. No. GB0908938.4; dated Mar. 1, 2011 (received by our Agent on Mar. 3, 2011); pp. 1-5.
Rospierski, Jeffrey; United States Design Patent; US D654,743 S; dated Feb. 28, 2012; 7 pages.
State Intellectual Property Office of P.R.C.; Notification of the First Office Action; App. No. 2007/80040949.2 (PCT/US07/023129); dated Jul. 16, 2010 (received by our Agent on Mar. 19, 2012); pp. 1-5.
Korean Intellectual Property Office Notice of Allowance; App. No. 10-2008-7026821; dated Dec. 17, 2013 (received by our agent Dec. 24, 2013); 11 pages (pp. 6-11 are a machine translation as provided by our agent).
Korean Intellectual Property Office Notice of Preliminary Rejection; App. No. 10-2013-7032032; dated Jan. 17, 2014 (received by our agent Jan. 20, 2014); 11 pages (pp. 7-11 are a machine translation as provided by our agent).
Koren Intellectual Property Office Notice of Preliminary Rejection; App. No. 10-2013-7033786; dated Jan. 24, 2014; 8 pages (pp. 5-8 are a machine translation as provided by our agent).
Korean Intellectual Property Office Notice of Preliminary Rejection; App. No. 10-2013-7033786; dated Jul. 2, 2014 (received by our agent Jul. 3, 2014); 8 pages (pp. 1-4 are a machine translation as provided by our agent).
Korean Intellectual Property Office Notice of Final Rejection; App. No. 10-2014-7010355; dated Jul. 2, 2014 (received by our agent Jul. 3, 2014); 9 pages (pp. 1-5 are a machine translation as provided by our agent).
Korean Intellectual Property Office; Notice of Preliminary Rejection; App. No. 10-2008-7026850; dated Jul. 10, 2013; 7 pages (and including machine translation consisting of 6 pages).
Korean Intellectual Property Office; Notice of Preliminary Rejection; App. No. 10-2008-7026821; dated Jun. 19, 2013; 3 pages (and including machine translation consisting of 3 pages).

\* cited by examiner

METHODS AND SYSTEMS FOR STERILIZATION

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC § 119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 11/396,256, entitled STERILIZATION METHODS AND SYSTEMS, naming Edward K. Y. Jung, Royce A. Levien, Robert W. Lord, Mark A. Malamud, John D. Rinaldo, Jr., and Lowell L. Wood, Jr. as inventors, filed 31 Mar. 2006, now U.S. Pat. No. 8,277,724 or is an application of which a currently co-pending application is entitled to the benefit of the filing date.

For purposes of the USPTO extra-statutory requirements, the present application constitutes a continuation-in-part of U.S. patent application Ser. No. 11/411,207, entitled SURVEYING STERILIZER METHODS AND SYSTEMS, naming Roderick A. Hyde, Edward K. Y. Jung, Royce A. Levien, Robert W. Lord, Mark A. Malamud, John D. Rinaldo, Jr., Clarence T. Tegreene, and Lowell L. Wood Jr. as inventors, filed 25 Apr. 2006, now U.S. Pat. No. 7,638,090 or is an application of which a currently co-pending application is entitled to the benefit of the filing date.

For purposes of the USPTO extra-statutory requirements, the present application constitutes a continuation-in-part of U.S. patent application Ser. No. 11/414,743, entitled METHODS AND SYSTEMS FOR MONITORING STERILIZATION STATUS, naming Edward K. Y. Jung, Royce A. Levien, Robert W. Lord, Mark A. Malamud, John D. Rinaldo, Jr., and Lowell L. Wood Jr. as inventors, filed 28 Apr. 2006, now U.S. Pat. No. 8,114,342 or is an application of which a currently co-pending application is entitled to the benefit of the filing date.

For purposes of the USPTO extra-statutory requirements, the present application constitutes a continuation-in-part of U.S. patent application Ser. No. 11/440,460, entitled METHODS AND SYSTEMS FOR STERILIZATION, naming Edward K. Y. Jung; Royce A. Levien; Robert W. Lord; Mark A. Malamud; John D. Rinaldo, Jr. and Lowell L. Wood, Jr. as inventors, filed 23 May 2006, now abandoned or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present applicant entity has provided above a specific reference to the application(s) from which priority is being claimed as recited by statute. Applicant entity understands that the statute is unambiguous in its specific reference language and does not require either a serial number or any characterization, such as "continuation" or "continuation-in-part," for claiming priority to U.S. patent applications. Notwithstanding the foregoing, applicant entity understands that the USPTO's computer programs have certain data entry requirements, and hence applicant entity is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

The present disclosure relates to sterilization methods and systems that may be used within numerous contexts, such as health-care and manufacturing facilities.

SUMMARY

In some embodiments a method is provided that includes applying one or more sterilization agents to one or more objects and transmitting one or more signals associated with one or more sterilization indicators that are associated with the one or more objects. In addition to the foregoing, other method aspects are described in the claims, drawings, and text forming a part of the present disclosure.

In some embodiments a method is provided that includes receiving one or more signals associated with one or more sterilization units and reconfiguring one or more sterilization indicators that are associated with one or more objects in accordance with the one or more signals. In addition to the foregoing, other method aspects are described in the claims, drawings, and text forming a part of the present disclosure.

In some embodiments a system is provided that includes circuitry for applying one or more sterilization agents to one or more objects and circuitry for transmitting one or more signals associated with one or more sterilization indicators that are associated with the one or more objects. In addition to the foregoing, other system aspects are described in the claims, drawings, and text forming a part of the present disclosure.

In some embodiments a system is provided that includes circuitry for receiving one or more signals associated with one or more sterilization units and circuitry for reconfiguring one or more sterilization indicators that are associated with one or more objects in accordance with the one or more signals. In addition to the foregoing, other system aspects are described in the claims, drawings, and text forming a part of the present disclosure.

In some embodiments a system is provided that includes means for applying one or more sterilization agents to one or more objects and means for transmitting one or more signals associated with one or more sterilization indicators that are associated with the one or more objects. In addition to the foregoing, other system aspects are described in the claims, drawings, and text forming a part of the present disclosure.

In some embodiments a system is provided that includes means for receiving one or more signals associated with one or more sterilization indicators that are associated with one or more objects and means for reconfiguring the one or more sterilization indicators in accordance with the one or more signals. In addition to the foregoing, other system aspects are described in the claims, drawings, and text forming a part of the present disclosure.

In some embodiments a method is provided that includes positioning one or more objects in operable proximity to one or more sterilization units and transmitting one or more signals associated with one or more sterilization indicators that are associated with the one or more objects. In addition to the foregoing, other method aspects are described in the claims, drawings, and text forming a part of the present disclosure.

In some embodiments a method is provided that includes receiving one or more signals associated with one or more sterilization indicators and applying one or more sterilization agents to one or more objects associated with the one or more sterilization indicators. In addition to the foregoing, other method aspects are described in the claims, drawings, and text forming a part of the present disclosure.

In some embodiments, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer. In addition to the foregoing, other system aspects are described in the claims, drawings, and/or text forming a part of the present application.

The foregoing summary is illustrative only and is not intended to be in any way limiting. In addition to the illustrative aspects, embodiments, and features described above, further aspects, embodiments, and features will become apparent by reference to the drawings, claims, and the following detailed description.

DETAILED DESCRIPTION

Figure 1:
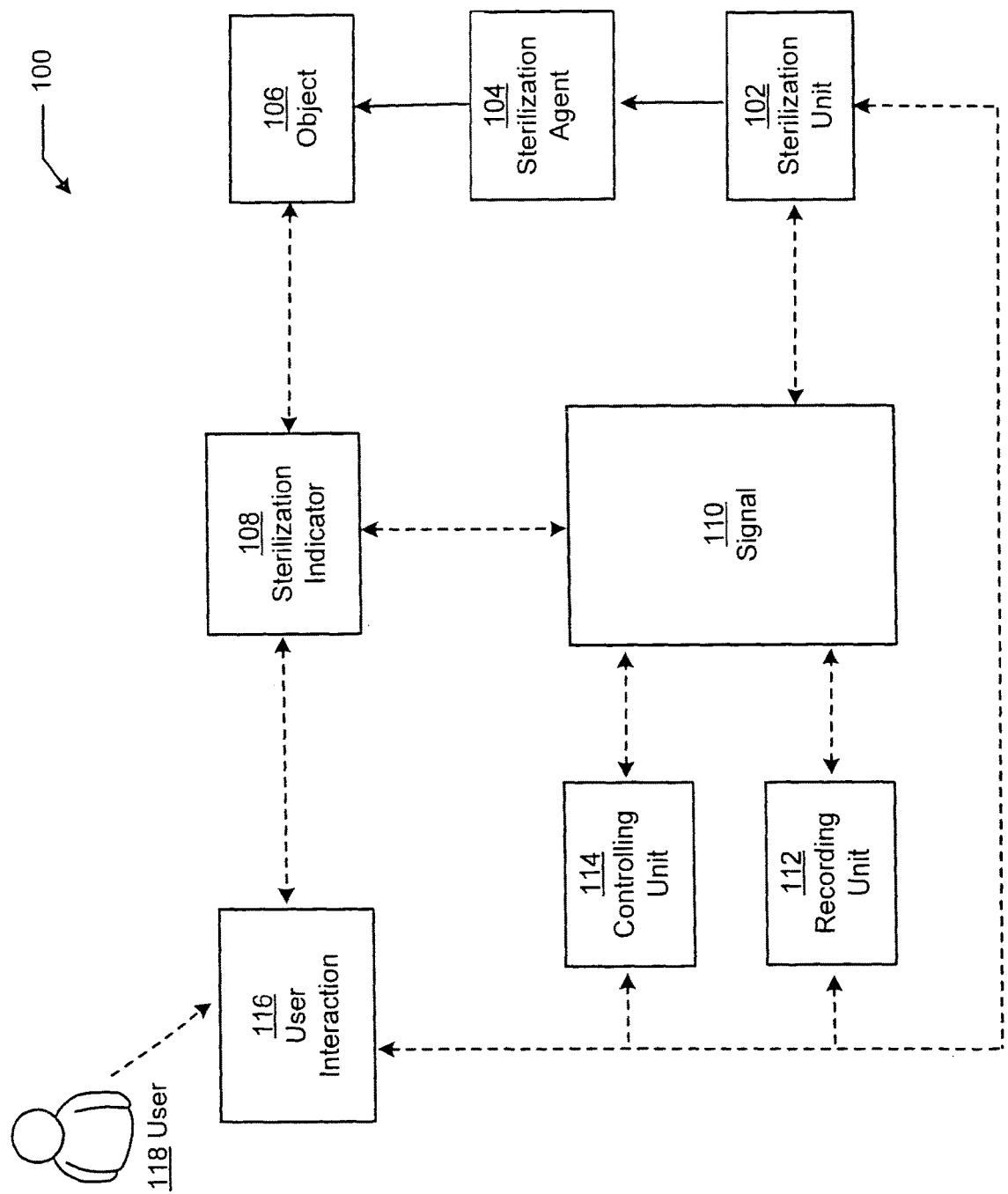
FIG. 1 illustrates an example system 100 in which embodiments may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

FIG. 1 illustrates an example system 100 in which embodiments may be implemented. In some embodiments, the system 100 is operable to provide a sterilization method. In some embodiments, one or more sterilization units 102 may apply one or more sterilization agents 104 to one or more objects 106. In some embodiments, one or more sterilization indicators 108 are associated with one or more objects 106. In some embodiments, one or more signals 110 are associated with one or more sterilization indicators 108. In some embodiments, one or more signals 110 are associated with one Or more sterilization units 102. In some embodiments, one or more signals 110 are associated with one or more recording units 112. In some embodiments, one or more signals 110 are associated with one or more controlling units 114. In some embodiments, system 100 provides user interaction 116 for one or more users 118. In some embodiments, one or more users 118 may interact with one or more sterilization indicators 108. In some embodiments, one or more users 118 may interact with one or more controlling units 114. In some embodiments, one or more users 118 may interact with one or more recording units 112. In some embodiments, one or more users 118 may interact with one or more sterilization units 102. In some embodiments, one or more users 118 may interact with one or more sterilization indicators 108, one or more controlling units 114, one or more recording units 112, one or more sterilization units 102 and/or substantially any combination thereof.

Sterilization Units

The system 100 can include one or more sterilization units 102. In some embodiments, one or more sterilization units 102 can apply one or more sterilization agents 104 to one or more objects 106. In some embodiments, one or more sterilization units 102 may emit radiation. In some embodiments, one or more sterilization units 102 may emit sterilizing radiation. Sterilizing radiation may be emitted from numerous types of sources that include, but are not limited to, emission from a cobalt-60 source, coherent light emitted from one or more frequency quadrupled-Nd YAG/glass lasers (neodymium-doped yttrium aluminum garnet (Nd:$Y_3Al_5O_{12}$), excimer lasers, frequency quadrupled diode pumped solid state (DPSS) lasers, incoherent light emitted from one or more low-pressure mercury resonance lamps, emission from tunable dye lasers, and the like. Sources of sterilizing radiation are known in the art and are commercially available (XENON Corporation, Wilmington, Mass.; Big Sky Laser Technologies, Inc., Bozeman, Mont.; Enhance-It, LLC, Hilton Head Island, S.C. 29926; Advanced Sterilization Products, Irvine, Calif. 92618; Coherent Inc., Santa Clara, Calif. 95054).

In some embodiments, one or more sterilization units 102 can emit sterilizing radiation substantially constantly. In some embodiments, one or more sterilization units 102 can emit sterilizing radiation as a pulse. In some embodiments, one or more sterilization units 102 can emit numerous types and/or combinations of sterilizing radiation, such as ultraviolet light and/or gamma radiation. In some embodiments, one or more sterilization units 102 can emit ultraviolet light having wavelengths between 100 nanometers and 400 nanometers and/or substantially any combination of wavelengths between 100 nanometers and 400 nanometers. In other embodiments, one or more sterilization units 102 can emit ultraviolet light having wavelengths between 180 nanometers and 300 nanometers and/or substantially any combination of wavelengths between 180 nanometers and 300 nanometers. In some embodiments, one or more sterilization units 102 can emit ultraviolet light having wavelengths between 255 nanometers and 280 nanometers and/or substantially any combination of wavelengths between 255 nanometers and 280 nanometers. In some embodiments, one or more sterilization units 102 can emit ultraviolet light having wavelengths between 250 nanometers and 280 nanometers and/or substantially any combination of wavelengths between 250 nanometers and 280 nanometers. In other embodiments, one or more sterilization units 102 can emit ultraviolet light having wavelengths that are centered, but asymnmetric, and about 265 nanometers and/or substantially any combination of wavelengths of such light. In some embodiments, one or more sterilization units 102 can exclude the emission of one or more wavelengths of radiation.

In some embodiments, one or more sterilization units 102 can emit sterilizing radiation according to parameters set at the one or more sterilization units 102. In some embodiments, one or more sterilization units 102 can emit sterilizing radiation according to instructions included within one or more signals 110 received by the one or more sterilization units 102. In some embodiments, one or more sterilization units 102 can emit sterilizing radiation according to parameters set at the one or more sterilization units 102 and according to instructions included within one or more signals 110 received by the one or more sterilization units 102. In some embodiments, emission of sterilizing radiation from one or more sterilization units 102 can be started and stopped, intensity modulated, paused, initiated, interrupted, resumed, steered, shaped, programmed to follow a preprogrammed schedule, routine or sequence, or substantially any combination thereof.

In some embodiments, one or more sterilization units 102 can emit one or more forms of non-sterilizing radiation. Examples of such non-sterilizing radiation include visible light, infrared radiation, sonic radiation, ultrasonic radiation, and the like.

In some embodiments, one or more sterilization units 102 can steer radiation emitted from the one or more sterilization units 102. In some embodiments, one or more sterilization units 102 can shape radiation emitted from the one or more sterilization units 102. In some embodiments, one or more sterilization units 102 can steer and shape radiation emitted from the one Or more sterilization units 102. Methods and systems that can be used to steer and/or and shape emitted radiation, such as ultraviolet light, are known (i.e., U.S. Patent Application Number 20030081293: Optical communications system and method; U.S. Patent Application Number 20020158814: Electronically scanned beam display; U.S. Pat. No. 6,755,536: System and method for displaying/projecting a color image; U.S. Pat. No. 6,937,221: Scanned beam display; U.S. Pat. No. 5,557,444: Miniature optical scanner for a two axis scanning system; all of which are incorporated herein by reference). Briefly, in some embodiments, one or more sterilization units 102 may include a moving mirror that is mounted to a spring plate. The mirror may be mounted with a ferromagnetic material that is driven by a pair of electromagnetic coils to provide motive force to the mirror. Drive electronics can provide an electrical signal to activate the coils and thereby move the mirror. Alternatively, a mirror may be mounted to a pivoting shaft and driven by an inductive coil. In operation, one or more sterilization units 102 may emit radiation that strikes a mirror and is deflected from the mirror into one or more objects 106. The path of the deflected radiation may be controlled through activation of drive electronics that activate the coils and thereby move the mirror. Numerous other methods and systems may be used to steer and shape radiation, such as radiation emitted from one or more sterilization units 102.

Sterilization Agents

The system 100 may include one or more sterilization agents 104. Numerous types of sterilization agents 104 malt be used within system 100. Examples of such sterilization agents 104 include, but are not limited to, ultraviolet light, gamma radiation, sonic radiation, chemicals, infrared radiation, steam, gases, and the like. Numerous types of sterilization agents 104 are known and are commercially available. Additional examples of such sterilization agents 104 include, but are not limited to, alcohol, ethylene oxide, ozone, ozonated water, ultraviolet light, gamma radiation, heat, steam, heat and pressure, chlorine, ammonia, and the like. In some embodiments, the identity of one or more sterilization agents 104 can be specified according to the identity and/or characteristics of one or more objects 106 to be sterilized. For example, in some embodiments, a sterilization agent 104 that is a gas may be applied to one or more objects 106. In other embodiments, ultraviolet light may be used as a sterilization agent 104 to sterilize one or more objects 106. Accordingly, one or more sterilization units 102 may apply one or more sterilization agents 104 in accordance with the characteristics of one or more objects 106 to be sterilized. In some embodiments, one or more sterilization agents 104 can be selected based on the type of contaminant that is to be killed, inactivated and/or detoxified through use of one or more sterilization agents 104. Examples of such contaminants can include, but are not limited to, bacteria, fungus, viruses, spores, microbes, eggs, and the like. The quantity and amount of time that one or more sterilization agents 104 are to be applied to one or more objects 106 to sanitize, kill, inactivate, and/or detoxify one or more contaminants can be readily determined though use of standard-protocols. Example irradiation parameters for ultraviolet light are provided in Table I for numerous types of contamination.

TABLE I

Sample Parameters for Sterilization with Ultraviolet Purifiers

| Bacteria | Energy in mW-sec/cm$^2$ Sterilization up to 90% | Energy in mW-sec/cm$^2$ Sterilization up to 99% |
|---|---|---|
| *Bacillus anthracis* | 4.52 | 9.04 |
| *S. enteritidis* | 4.00 | 8.00 |
| *B. megatherium* sp.(vegetative) | 1.30 | 2.60 |
| *B. megatherium* sp.(spores) | 2.73 | 5.46 |
| *B. paratyphosus* | 3.20 | 6.40 |
| *B. subtilis* | 7.10 | 14.20 |
| *B. subtilis* spores | 12.00 | 24.00 |
| *Corynebacterium diphtheriae* | 3.37 | 6.74 |
| *Eberthella typhosa* | 2.14 | 4.28 |
| *Escherichia coli* | 3.00 | 6.00 |
| *Micrococcus candidus* | 6.05 | 12.10 |
| *Micrococcus sphaeroides* | 10.00 | 20.00 |
| *Neisseria catarrhalis* | 4.40 | 8.80 |
| *Phytomonas tumefaciens.* | 4.40 | 8.80 |
| *Proteus vulgaris* | 2.64 | 5.28 |
| *Pseudomonas aeruginosa* | 5.50 | 11.00 |
| *Pseudomonas fluorescens* | 3.50 | 7.00 |
| *S. typhimurium* | 8.00 | 16.00 |
| *Sarcina Lutea* | 19.70 | 39.40 |
| *Seratia marcescens* | 2.42 | 4.84 |
| *Dysentery bacilli* | 2.20 | 4.40 |
| *Shigella paradysenteriae* | 1.68 | 3.36 |
| *Spirillum rubrum* | 4.40 | 8.80 |
| *Staphylococcus albus* | 1.84 | 3.68 |
| *Staphylococcus aureus* | 2.60 | 5.20 |
| *Streptococcus hemolyticus* | 2.16 | 4.32 |
| *Streptococcus lactis* | 6.15 | 12.30 |
| *Streptococcus viridans* | 2.00 | 4.00 |

Objects

Numerous types of objects 106 may be used within system 100. In some embodiments, one or more sterilization agents 104 are applied to the one or more objects 106. In some embodiments, one or more sterilization agents 104 are not applied to the one or more objects 106. Examples of such objects 106 include, but are not limited to, humans, non-human animals, plants, medical instruments, cooking utensils, food storage devices, pharmaceutical formulation devices, food packaging devices, food preparation devices, eating utensils, dental instruments, and the like. In some embodiments, one or more objects 106 include one or more portions of a human body. For example, in some embodiments, one or more objects 106 include one or more hands, arms, feet, legs, and substantially any combination thereof. In some embodiments, the one or more portions of a human body are covered. For example, in some embodiments, one or more hands are covered with gloves. In some embodiments, one or more objects 106 are included within packaging material.

Sterilization Indicators

Numerous types of sterilization indicators 108 may be used within system 100. In some embodiments, one or more sterilization indicators 108 may be physically coupled to one or more objects 106. In some embodiments, one or more sterilization indicators 108 are not physically coupled to one or more objects 106. For example, in some embodiments, one or more sterilization indicators 108 may be located in one or more remote locations from the one or more objects 106 with which they are associated. In some embodiments, one Or more sterilization indicators 108 may be physically coupled with one or more objects 106 and one or more sterilization indicators may be remote from the one or more objects 106 with which they are associated.

Sterilization indicators 108 may utilize numerous technologies. Examples of such technologies include, but are not limited to, fluorescent indicators, radio frequency signals 110, magnetic properties, color changes of chemical indicators, optical signals 110, bar codes, and the like. Use of such detection methods are known and have been described (i.e., U.S. Pat. No. 6,485,979: Electronic system for tracking and monitoring articles to be sterilized and associated method, herein incorporated by reference).

Sterilization indicators 108 may be configured into numerous confirmations. For example, in some embodiments, one or more sterilization indicators 108 may be configured as a bracelet, ring, identification card, badge, glove, foot covering, coat, stamp (such as a stamp that includes a magnetic or fluorescent dye), and the like. In some embodiments, sterilization indicators 108 may be configured for single use. For example, in some embodiments, one or more sterilization indicators 108 may be configured as a bracelet that forms a breakable junction upon attachment to an object, such as a human wrist. Accordingly, in some embodiments, the bracelet is broken and made inoperable upon removal from the object following use. In some embodiments, one or more sterilization indicators 108 are reusable. For example, in some embodiments, one or more sterilization indicators 108 may be included within one or more reusable gloves.

In some embodiments, one or more sterilization indicators 108 may communicate with one or more sterilization units 102. In some embodiments, one or more sterilization indicators 108 may communicate with one or more controlling units 114. In some embodiments, one or more sterilization indicators 108 may communicate with one or more recording units 112. In some embodiments, one or more sterilization indicators 108 may provide for user interaction 116 with one or more users 118. In some embodiments, one or more sterilization indicators 108 may receive one or more signals 110. In some embodiments, one or more sterilization indicators 108 may transmit one or more signals 110. In some embodiments, one or more sterilization indicators 108 may receive one or more signals 110 and transmit one or more signals 110.

Signals

The system 100 includes one or more signals 110. The one or more signals 110 can include numerous types of information. In some embodiments, one or more signals 110 can include one or more instructions for one or more sterilization units 102 to apply one or more sterilization agents 104 to one or more objects 106. In some embodiments, one or more signals 110 can include one or more instructions for one or more sterilization units 102 to avoid applying one or more sterilization agents 104 to one or more objects 106. In some embodiments, one or more signals 110 are associated with one or more instructions for one or more sterilization units 102 to comply with one or more sterilization protocols. In some embodiments, one or more signals 110 are associated with one or more sterilization statuses assigned to one or more objects 106. In some embodiments, one or more signals 110 are associated with one or more parameters associated with application of one or more sterilization agents 104 to one or more objects 106.

In some embodiments, one or more signals 110 are transmitted to one or more sterilization units 102. In some embodiments, one or more signals 110 are transmitted from one or more sterilization units 102. In some embodiments, one or more signals 110 are transmitted to one or more sterilization indicators 108. In some embodiments, one or more signals 110 are transmitted from one or more sterilization indicators 108. In some embodiments, one or more signals 110 are transmitted to one or more recording units 112. In some embodiments, one or more signals 110 are transmitted from one or more controlling units 114. In some embodiments, one or more signals 110 are transmitted to one or more controlling units 114.

In some embodiments, one or more signals 110 are transmitted to one or more sterilization units 102 from one or more sterilization indicators 108 that are physically coupled to one or more objects 106. In some embodiments, one or more signals 110 are transmitted to one or more sterilization units 102 from one or more sterilization indicators 108 that are not physically coupled to one or more objects 106. In some embodiments, one or more signals 110 are transmitted to one or more sterilization units 102 from one or more sterilization indicators 108 that are remote from one or more objects 106. In some embodiments, one or more signals 110 are transmitted from one or more sterilization units 102 to one or more sterilization indicators 108 that are physically coupled to one or more objects 106. In some embodiments, one or more signals 110 are transmitted from one or more sterilization units 102 to one or more sterilization indicators 108 that are not physically coupled to one or more objects 106. In some embodiments, one or more signals 110 are transmitted from one or more sterilization units 102 to one or more sterilization indicators 108 that are remote from one or more objects 106.

In some embodiments, one or more signals 110 are associated with one or more recording units 112. In some embodiments, one or more signals 110 are associated with one or more controlling units 114. In some embodiments, one Or more signals 110 are associated with one or more sterilization indicators 108. In some embodiments, one or more signals 110 are associated with one or more sterilization units 102.

Numerous types of signals may be transmitted. Examples of such signals include, but are not limited to, hardwired signals, wireless signals, infrared signals, optical signals, radiofrequency (RF) signals, auditory signals, digital signals, analog signals, or substantially any combination thereof.

Recording Units

The system 100 may include one or more recording units 112. In some embodiments, one or more recording units 112 communicate with one or more sterilization units 102, one or more sterilization indicators 108, one or more users 118, one or more controlling units 114 and/or substantially any combination thereof. In some embodiments, one or more recording units 112 provide for user interaction 116 by one or more users 118. In some embodiments, one or more recording units 112 can receive one or more signals 110. The one or more recording units 112 can record numerous types of information. In some embodiments, one or more recording units 112 record information associated with one or more sterilization protocols associated with one or more objects 106. In some embodiments, one or more recording units 112 record one or more times when one or more objects 106 are sterilized. In some embodiments, one or more recording units 112 record the identity of one or more sterilization agents 104 that were applied to one or more objects 106. In some embodiments, one or more recording units 112 record the intensity with which one or more objects 106 were sterilized. In some embodiments, one or more recording units 112 record the frequency with which one or more objects 106 are sterilized. Many types of recording units 112 may be used. Examples of such recording devices include, but are not limited to, many types of memory, optical disks, magnetic disks, magnetic tape, and the like.

Controlling Units

System 100 may include one or more controlling units 114. Controlling units 114 may be coupled to numerous devices to provide for control of the devices by system 100. For example, in some embodiments, one or more controlling units 114 can be coupled to one or more door locks to allow one or more objects 106 to enter into, or exit from, one or more areas. In some embodiments, one or more controlling units 114 may be designed as switches that control usage of one or more devices. For example, in some embodiments, one or more controlling units 114 may be installed within a medical device such that the medical device will only operate if it has been sterilized.

User Interaction

The system 100 may provide for user interaction 116. In some embodiments, a user 118 may interact with one or more sterilization units 102, one or more recording units 112, one or more controlling units 114, one or more sterilization indicators 108 and/or substantially any combination thereof. Such interactions can include, but are not limited to, inputting instructions related to the sterilization of one or more objects 106 with regard to time, place, duration, intensity, priority, identity of one or more sterilization agents 104 and/or substantially any combination thereof.

The user 118 can interact through use of numerous technologies. For example, user interaction 116 can occur through use of hardwired methods, such as through use of a keyboard, use of wireless methods, use of the internet, and the like. In some embodiments, a user 118 is human. In some embodiments, a user 118 is not human.

In some embodiments, a sterilization method involves completely sterilizing one or more objects 106 and/or partially sterilizing one or more objects 106. In other embodiments, the method includes avoiding sterilization of one or more objects 106. In some embodiment, a method includes sanitizing one or more objects 106.

Figure 2:
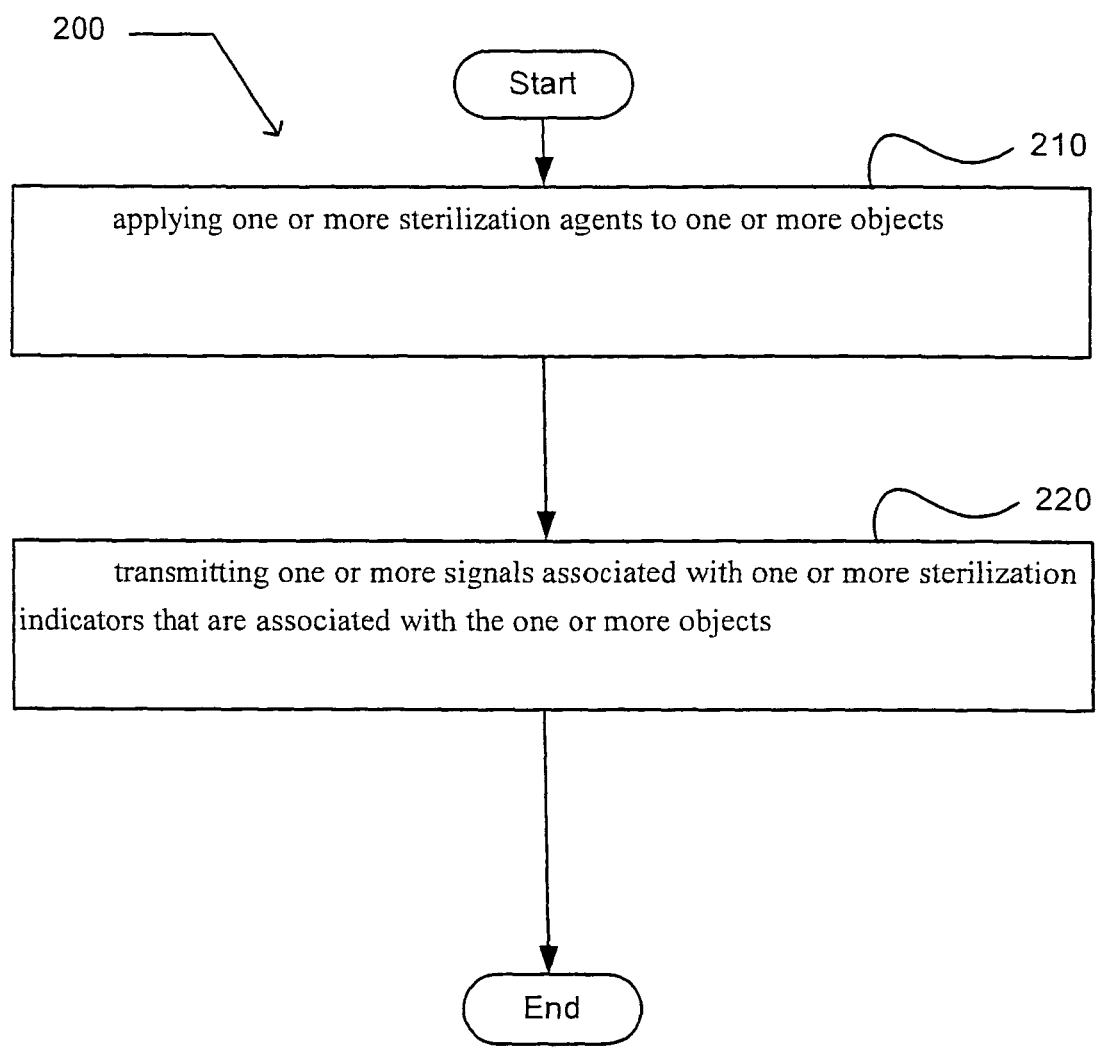
FIG. 2 illustrates an operational flow representing example operations related to sterilization methods.

FIG. 2 illustrates an operational flow 200 representing examples of operations that are related to the performance of a sterilization method. In FIG. 2 and in following figures that include various examples of operations used during performance of the sterilization method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 200 includes an applying operation 210 involving applying one or more sterilization agents to one or more objects. In some embodiments, one or more sterilization units 102 may apply one or more sterilization agents 104 to one or more objects 106. In some embodiments, the one or more sterilization units 102 may be mobile. For example, in some embodiments, the one or more sterilization units 102 may be positioned on a cart that may be transported throughout a facility such as a hospital, food processing facility, pharmaceutical manufacturing facility, dental office, and the like. In some embodiments, the one or more sterilization units 102 may be immobile. For example, in some embodiment, the one or more sterilization units 102 may be mounted on a wall of a hospital, food processing facility, pharmaceutical manufacturing facility, dental office, and the like.

In some embodiments one or more sterilization units 102 may apply one type of sterilization agent 104 to one or more objects 106. In some embodiments, one or more sterilization units 102 may apply one or more types of sterilization agents 104 to one or more objects 106. One or more sterilization units 102 may apply numerous types of sterilization agents 104 to one or more objects 106. Examples of such sterilization agents 104 include, but are not limited to, ultraviolet light, gamma radiation, sonic radiation, chemicals, infrared radiation, steam, gases, and the like. Numerous types of sterilization agents 104 are known and are commercially available.

In some embodiments, one or more sterilization units 102 may apply additional materials to one or more objects 106 that are not sterilizing agents. For example, in some embodiments, one or more sterilization units 102 may rinse one or more objects 106 with water. In some embodiments, one or more sterilization units 102 may blow air onto one or more objects 106 to dry the one or more objects 106. In some embodiments, one or more sterilization units 102 may apply one or more sterilization indicators 108 to one or more objects 106 to indicate that the one or more objects 106 were sterilized. For example, in some embodiments, one or more sterilization units 102 may apply one or more sterilization indicators 108 that are dyes to one or more objects 106 following sterilization of the one or more objects 106.

One or more sterilization units 102 may apply one or more sterilization agents 104 to numerous types of objects 106. In some embodiments, the one or more objects 106 are medical instruments. In some embodiments, the one or more objects 106 are dental instruments. In some embodiments, the one or more objects 106 are humans. In some embodiments, the one or more objects 106 are portions of a human. For example, in some embodiments, the one or more objects 106 are human hands. Accordingly, the one or more sterilization units 102 may apply one or more sterilization agents 104 to one or more human hands.

The operational flow 200 also includes a transmitting operation 220 involving transmitting one or more signals associated with one or more sterilization indicators that are associated with the one or more objects. In some embodiments, one or more sterilization units 102 transmit one or more signals 110 associated with one or more sterilization indicators 108 that are associated with one or more objects 106. In some embodiments, one or more sterilization units 102 may transmit one or more signals 110 to one or more sterilization indicators 108 that are physically coupled to one or more objects 106. In some embodiments, one or more sterilization units 102 may transmit one or more signals 110 to one or more sterilization indicators 108 that are not physically coupled to one or more objects 106. In some embodiments, one or more sterilization units 102 may transmit one or more signals 110 associated with the type or types of sterilization agents 104 that were applied to one or more objects 106. In some embodiments, one or more sterilization units 102 may transmit one or more signals 110 associated with the frequency with which one or more sterilization agents 104 were applied to one or more objects 106. In some embodiments, one or more sterilization units 102 may transmit one or more signals 110 associated with the intensity with which one or more sterilization agents 104 were applied to one or more objects 106. In some embodiments, one or more sterilization units 102 may transmit one or more signals 110 which indicate that the one or more objects 106 were sterilized in accordance with one or more protocols. In some embodiments, one or more sterilization units 102 may transmit one or more signals 110 which indicate that the one or more objects 106 have been sterilized in accordance with one or more protocols. In some embodiments, one or more sterilization units 102 may transmit one or more signals 110 which indicate that the one or more objects 106 have not been sterilized in accordance with one or more protocols. In some embodiments, one or more sterilization units 102 may transmit one or more signals 110 which associate one or more sterilization statuses with one or more objects 106. In some embodiments, one or more sterilization units 102 may transmit one or more signals 110 that change the sterilization status of one or more sterilization indicators 108 that are associated with one or more objects 106. In some embodiments, one or more sterilization units 102 may transmit one or more signals 110 associated with one or more recording units 112. In some embodiments, one or more sterilization units 102 may transmit one or more signals 110 associated with one or more controlling units 114.

Figure 3:
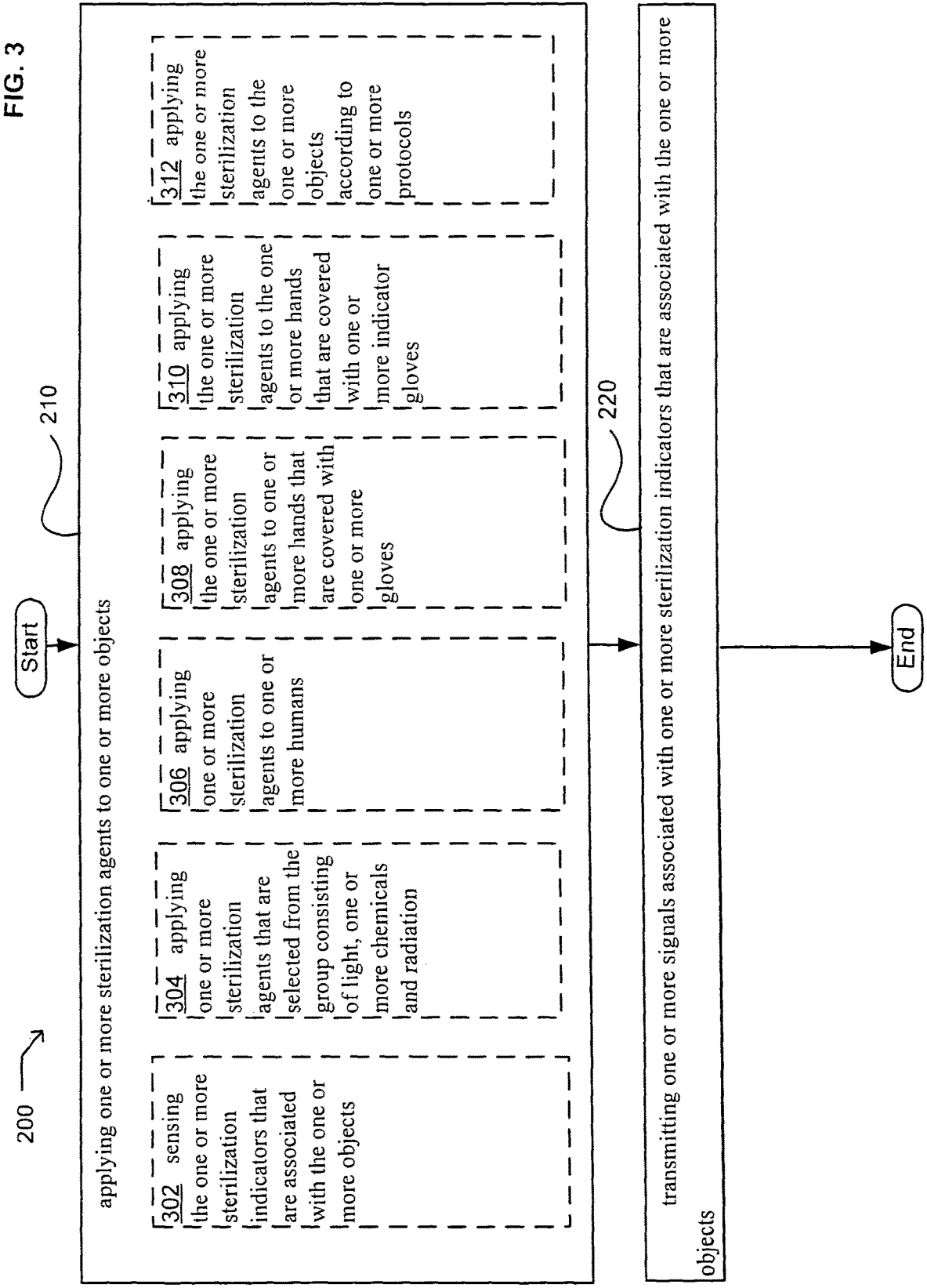
FIG. 3 illustrates an alternative embodiment of the example operation flow of FIG. 2.

FIG. 3 illustrates alternative embodiments of the example operational flow 200 of FIG. 2. FIG. 3 illustrates example embodiments where the applying operation 210 may include at least one additional operation. Additional operations may include an operation 302, operation 304, operation 306, operation 308, operation 310 and/or operation 312.

At operation 302, the applying operation 210 may include sensing one or more sterilization indicators 108 that are associated with one or more objects 106. In some embodiments, one or more sterilization units 102 may sense one or more sterilization indicators 108 that are associated with one or more objects 106. In some embodiments, one or more sterilization units 102 may sense the presence of one or more sterilization indicators 108 that are associated with one or more objects 106. In some embodiments, one or more sterilization units 102 may sense the absence of one or more sterilization indicators 108 that are associated with one or more objects 106. In some embodiments, one or more sterilization units 102 may determine what type or types of sterilization agents 104 to apply to one or more objects 106. In some embodiments, one Or more sterilization units 102 may determine what type or types of sterilization agents 104 not to apply to one or more objects 106. In some embodiments, one or more sterilization units 102 may determine whether to apply one or more sterilization agents 104 to one or more objects 106 in accordance with a sterilization protocol. In some embodiments, one or more sterilization units 102 may determine the intensity with which to apply one or more sterilization agents 104 to one or more objects 106. In some embodiments, one or more sterilization units 102 may determine the frequency with which to apply one or more sterilization agents 104 to one or more objects 106. In some embodiments, one or more sterilization units 102 may determine when one or more sterilization agents 104 were last applied to one or more objects 106. In some embodiments, one or more sterilization units 102 may determine when one or more sterilization agents 104 should be applied to one or more objects 106.

At operation 304, the applying operation 210 may include applying one or more sterilization agents 104 that are selected from the group consisting of light, one or more chemicals and radiation. In some embodiments, one or more sterilization units 102 apply one or more sterilization agents 104 that are selected from the group consisting of light, one or more chemicals and radiation. In some embodiments, one or more sterilization units 102 may apply one or more sterilization agents 104 that include light. In some embodiments, one or more sterilization units 102 apply sterilizing light. In some embodiments, one or more sterilization units 102 may apply ultraviolet light. In some embodiments, one or more sterilization units 102 may apply nonsterilizing light. For example, in some embodiments, visible light may be applied to one or more objects 106. In some embodiments, one or more sterilization units 102 apply one or more sterilization agents 104 that include one or more chemicals, Numerous types of chemicals may be applied by one or more sterilization units 102. In some embodiments, one or more chemicals may be applied that do not sterilize one or more objects 106. For example, in some embodiments, one or more chemicals that are sterilization indicators 108 may be applied to one or more objects 106. In some embodiments, one or more chemicals may be applied to one or more objects 106 that wash the one or more objects 106 without sterilizing the one or more objects 106. In some embodiments, one or more chemicals may be applied that sterilize one or more objects 106. Examples of such chemicals include, but are not limited to, alcohol, chlorine, ammonia, ozone, ethylene oxide, peroxides, acids, bases, and the like. In some embodiments, one or more sterilization units 102 apply one or more sterilization agents 104 that include one or more types of radiation. Examples of types of radiation include, but are not limited to, gamma radiation, infrared radiation, beta radiation, and the like. In some embodiments, one or more sterilization units 102 may apply one type of sterilization agent 104 to one or more objects 106. In some embodiments, one or more sterilization units 102 may apply one or more types of sterilization agents 104 to one or more objects 106.

At operation 306, the applying operation 210 may include applying one or more sterilization agents 104 to one or more humans. In some embodiments, one or more sterilization units 102 may apply one or more sterilization agents 104 to one or more humans. In some embodiments, one or more sterilization units 102 may apply one or more sterilization agents 104 to all accessible surfaces of one or more humans. For example, in some embodiments, one or more sterilization units 102 may be configured as a shower where one or more sterilization agents 104 may be applied to one or more humans. In some embodiments, the one or more humans may be covered with clothing or other protective wear. In some embodiments, the one or more humans may not be covered with clothing or other protective wear. In some embodiments, one or more sterilization units 102 may apply one or more sterilization agents 104 to one or more portions of a human. For example, in some embodiments, one or more sterilization units 102 are configured to apply one or more sterilization agents 104 to one or more feet. In some embodiments, one or more sterilization units 102 are configured to apply one or more sterilization agents 104 to one or more hands. In some embodiments, one or more sterilization units 102 are configured to apply one or more sterilization agents 104 to one or more arms and hands. In some embodiments, the one or more portions of one or more humans may be covered with clothing or other protective wear. In some embodiments, the one or more portions of one or more humans may not be covered with clothing or other protective wear.

At operation 308, the applying operation 210 may include applying one or more sterilization agents 104 to one or more hands that are covered with one or more gloves. In some embodiments, one or more sterilization units 102 may apply one or more sterilization agents 104 to one or more hands that are covered with one or more gloves. In some embodiments, one or more sterilization units 102 are configured as hand sterilizers to apply one or more sterilization agents 104 onto one or more hands. In some embodiments, one or more sterilization units 102 are configured to apply one or more gloves to one or more hands. For example, in some embodiments, one or more hands may be placed within one or more sterilization units 102 where gloves may be applied to the one or more hands by the one or more sterilization units 102. In some embodiments, rubber gloves may be stretched over one or more hands that are placed within one or more sterilization units 102. In other embodiments, one or more gloves may be formed on one or more hands through application of one or more coat forming compounds to the one or more hands. For example, in some embodiments, non-toxic paint may be sprayed onto one or more hands to form one or more gloves. In some embodiments, one or more coat forming compounds may be applied to one or more hands that are covered with gloves. For example, one or more hands may each be covered with a latex glove to which one or more coat forming compounds are applied. In some embodiments, metalized gloves are used to cover one or more hands. Numerous examples of metalized gloves are known and are commercially available (i.e., Newtex Industries, Inc., Victor, N.Y.). In some embodiments, one or more hands may be covered with one or more gloves that protect the one or more hands from one or more sterilization agents 104 that are applied to the one or more hands.

At operation 310, the applying operation 210 may include applying the one or more sterilization agents 104 to the one or more hands that are covered with one or more indicator gloves. In some embodiments, one or more sterilization units 102 may apply one or more sterilization agents 104 to one or more hands that are covered with one or more indicator gloves. In some embodiments, one or more indicator gloves indicate if one or more sterilization agents 104 were applied to the one or more indicator gloves. In some embodiments, one or more indicator gloves indicate when one or more sterilization agents 104 were applied to the one or more indicator gloves. In some embodiments, one or more indicator gloves indicate what type or types of sterilization agents 104 were applied to the one or more indicator gloves. In some embodiments, one or more indicator gloves indicate if one or more sterilization agents 104 should be applied to the one or more indicator gloves. Numerous technologies may be used to produce indicator gloves. In some embodiments, a phosphorescent dye may be included within the indicator gloves that will emit light upon being exposed to ultraviolet light. Accordingly, in some embodiments, such indicator gloves may be used to indicate the intensity with which the indicator gloves were irradiated with ultraviolet light. In some embodiments, such indicator gloves may be used to indicate when the indicator gloves were last irradiated with ultraviolet light. In some embodiments, indicator gloves may include one or more chemicals that change color upon being sterilized. Such chemicals are known and are commercially available (i.e., JP Laboratories, Inc., Middlesex, N.J.). In some embodiments, one or more indicator gloves may include one or more sterilization indicators 108.

At operation 312, the applying operation 210 may include applying one or more sterilization agents 104 to one or more objects 106 according to one or more protocols. In some embodiments, one or more sterilization units 102 may apply one or more sterilization agents 104 to one or more objects 106 according to one or more protocols. In some embodiments, one or more sterilization protocols may be associated with one or more objects 106. In some embodiments, a sterilization protocol may specify the immediacy, latency, intensity and time-integrated intensity of sterilizing radiation that is to be applied to one or more objects 106. In some embodiments, a sterilization protocol may specify one or more types of sterilization agents 104 that are to be applied to one or more objects 106. In some embodiments, a sterilization protocol may specify one or more types of sterilization agents 104 that are not to be applied to one or more objects 106. In some embodiments, a sterilization protocol may specify the frequency with which one or more sterilization agents 104 are to be applied to one or more objects 106. In some embodiments, a sterilization protocol may specify the intensity and/or concentration that one or more types of sterilization agents 104 that are to be applied to one or more objects 106. Numerous sterilization protocols can be assigned to one or more objects 106. In some embodiments, such protocols can be used to specify the intensity with which one or more objects 106 are sterilized to account for high patient-hazard and/or high infectivity use of the one or more objects 106 to ensure that such objects 106 receive rigorous and/or frequent sterilization treatment. Accordingly, in some embodiments, one or more sterilization indicators 108 can communicate with one or more sterilization units 102 to determine if one or more objects 106 have been sterilized in accordance with a sterilization protocol. In some embodiments, one or more sterilization indicators 108 can indicate how much time has passed since one or more objects 106 were last sterilized. In some embodiments, one or more sterilization indicators 108 can communicate with one or more sterilization units 102 to indicate when one or more objects 106 were last sterilized. In other embodiments, one or more sterilization indicators 108 can emit phosphorescent light from one or more phosphorescent materials included within one or more objects 106 to indicate when the one or more objects 106 were last sterilized. In some embodiments, one or more sterilization indicators 108 can communicate with one or more recording units 112 to indicate when one or more objects 106 were last sterilized. In some embodiments, one or more sterilization indicators 108 can communicate with one or more sterilization units 102 to determine when one or more objects 106 were last sterilized.

Figure 4:
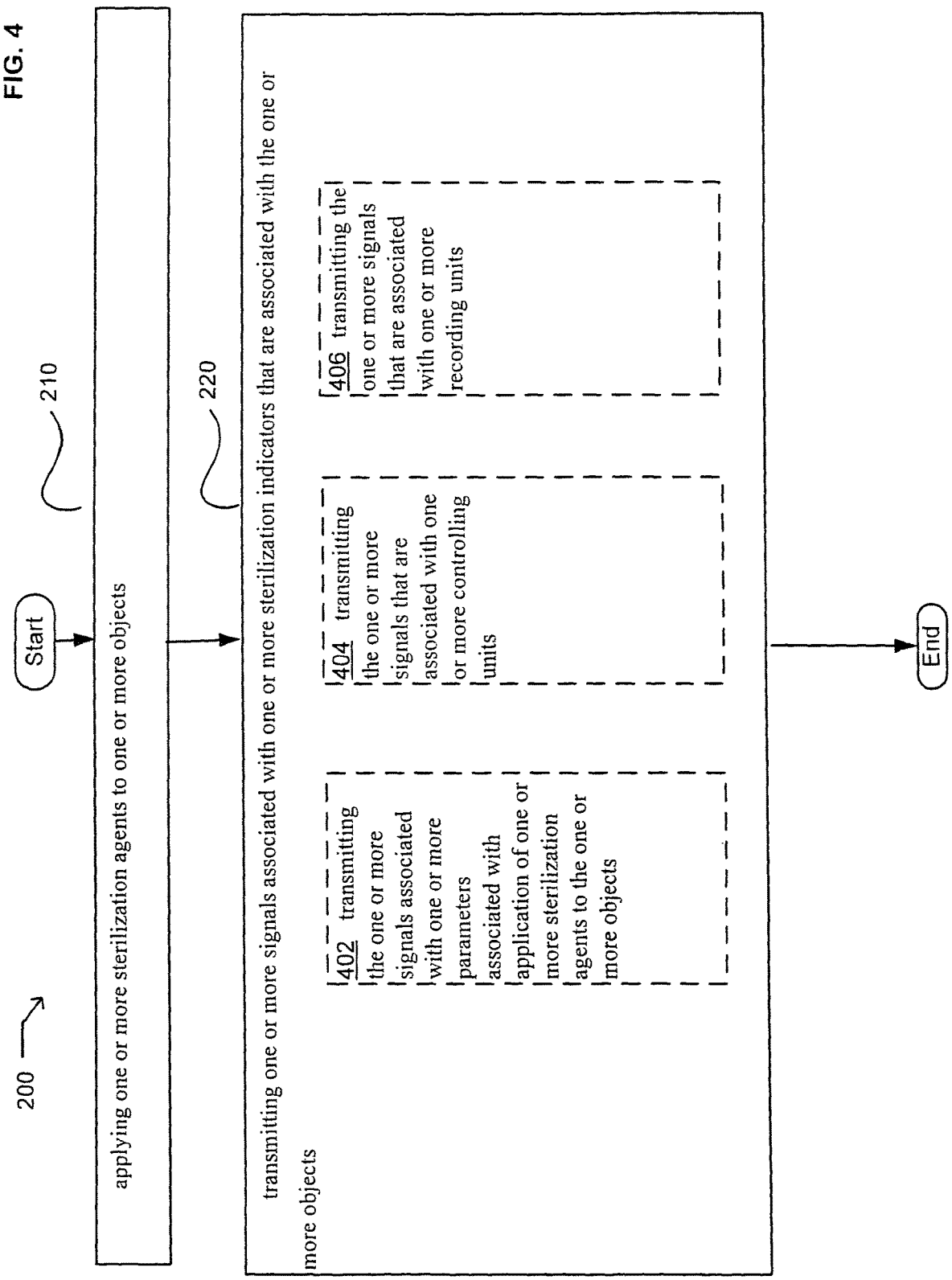
FIG. 4 illustrates an alternative embodiment of the example operation flow of FIG. 2.

FIG. 4 illustrates alternative embodiments of the example operational flow 200 of FIG. 2. FIG. 4 illustrates example embodiments where the transmitting operation 220 may include at least one additional operation. Additional operations may include an operation 402, operation 404 and/or operation 406.

At operation 402, the transmitting operation 220 may include transmitting one or more signals 110 associated with one or more parameters associated with application of one or more sterilization agents 104 to one or more objects 106. In some embodiments, one or more sterilization units 102 may transmit one or more signals 110 associated with one or more parameters associated with application of one or more sterilization agents 104 to one or more objects 106. In some embodiments, one or more sterilization units 102 may transmit one or more signals 110 associated with one or more times of application, one or more intensities of application, one or more frequencies of application, one or more durations of application, one or more types of sterilization agent 104 used for application, one or more protocols used for application, and/or substantially any combination thereof that was used to sterilize one or more objects 106.

At operation 404, the transmitting operation 220 may include transmitting one or more signals 110 that are associated with one or more controlling units 114. In some embodiments, one or more sterilization units 102 may transmit one or more signals 110 associated with one or more controlling units 114. In some embodiments, one or more sterilization units 102 may transmit one or more signals 110 that instruct the one or more controlling units 114 to act. In some embodiments, one or more sterilization units 102 may transmit one or more signals 110 that instruct the one or more controlling units 114 not to act. In some embodiments, one or more sterilization units 102 may transmit one or more signals 110 instructing one or more controlling units 114 to allow one or more objects 106 associated with one or more sterilization indicators 108 to enter into one or more spaces. In some embodiments, one or more sterilization units 102 may transmit one or more signals 110 instructing one or more controlling units 114 to disallow one or more objects 106 associated with one or more sterilization indicators 108 from entering one or more spaces. In some embodiments, one or more sterilization units 102 may transmit one or more signals 110 instructing one or more controlling units 114 to allow one or more objects 106 associated with one or more sterilization indicators 108 to exit from one or more spaces. In some embodiments, one or more sterilization units 102 may transmit one or more signals 110 instructing one or more controlling units 114 to disallow one or more objects 106 associated with one or more sterilization indicators 108 from exiting one or more spaces. In some embodiments, one or more sterilization units 102 may transmit one or more signals 110 to one or more devices which include one or more controlling units 114 that control operation of the device.

At operation 406, the transmitting operation 220 may include transmitting one or more signals 110 that are associated with one or more recording units 112. In some embodiments, one or more sterilization units 102 may transmit one or more signals 110 associated with one or more recording units 112. In some embodiments, one or more sterilization units 102 may transmit one or more signals 110 to one or more recording units 112 indicating compliance of one or more objects 106 with a sterilization protocol. In some embodiments, one or more sterilization units 102 may transmit one or more signals 110 to one or more recording units 112 indicating noncompliance of one or more objects 106 with a sterilization protocol. In some embodiments, one or more sterilization units 102 may transmit one or more signals 110 to one or more recording units 112 indicating movement of one or more objects 106 about one or more spaces. In some embodiments, one or more sterilization units 102 may transmit one or more signals 110 to one or more recording units 112 indicating one or more parameters associated with one or more objects 106. Numerous parameters associated with one or more objects 106 may be transmitted. In some embodiments, one or more sterilization units 102 may transmit one or more signals 110 associated with parameters associated with application of one or more sterilization agents 104 to one or more objects 106. Examples of such parameters include, but are not limited to, one or more times of application one or more intensities of application, one or more frequencies of application, one or more durations of application, one or more types of sterilization agents 104 used for application, one or more protocols used for application, and/or substantially any combination thereof that was used to sterilize one or more objects 106.

Figure 5:
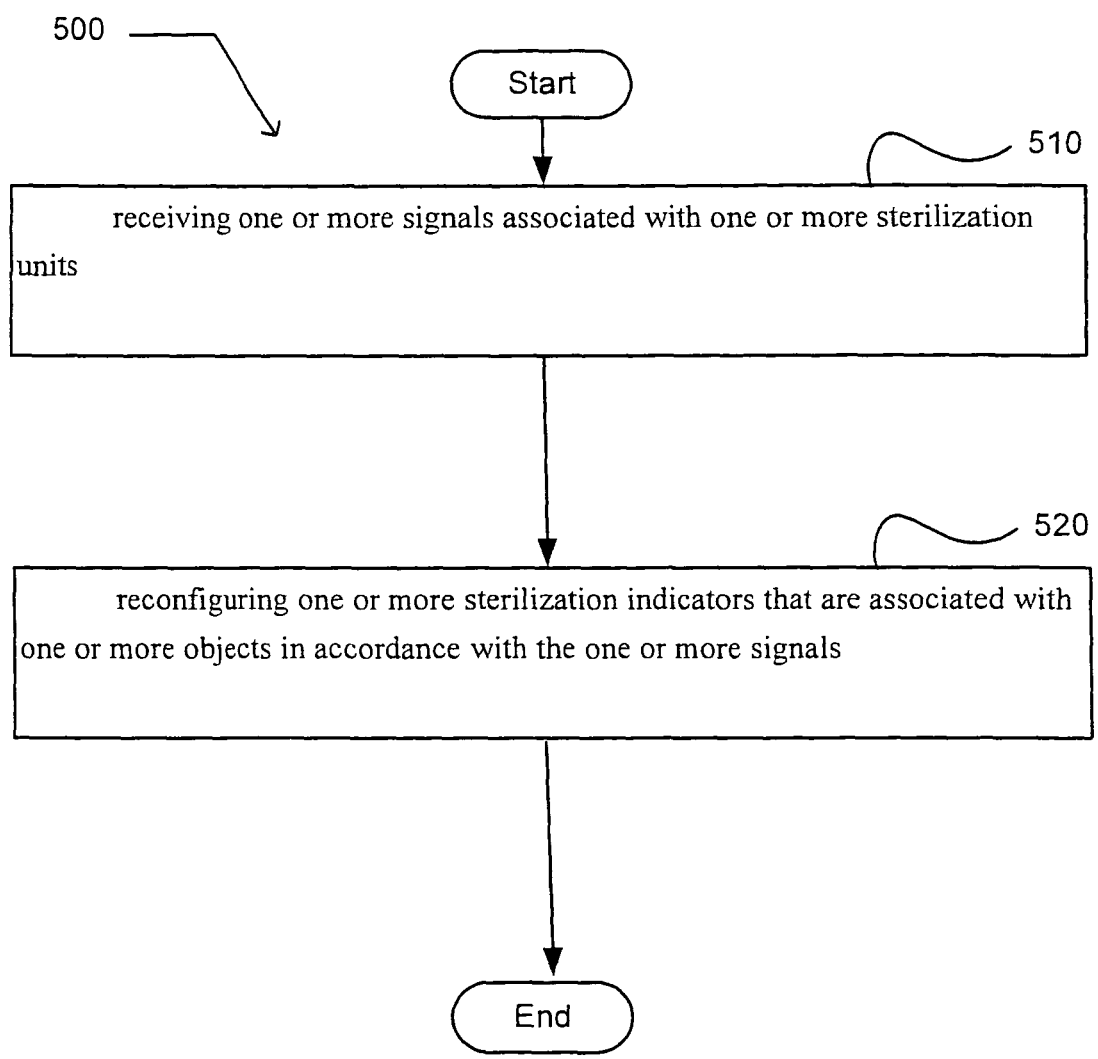
FIG. 5 illustrates an operational flow representing example operations related to sterilization methods.

FIG. 5 illustrates an operational flow 500 representing examples of operations that are related to the performance of a sterilization method. In FIG. 5 and in following figures that include various examples of operations used during performance of the sterilization method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 500 includes a receiving operation 510 involving receiving one or more signals associated with one or more sterilization units. In some embodiments, one or more sterilization indicators 108 receive one or more signals 110 associated with one or more sterilization units 102. In some embodiments, the one or more sterilization indicators 108 are physically coupled to one or more objects 106. In some embodiments, the one or more sterilization indicators 108 are not physically coupled to one or more objects 106. In some embodiments, one or more sterilization indicators 108 may receive one or more signals 110 associated with the type or types of sterilization agents 104 that were applied to one or more objects 106. In some embodiments, one or more sterilization indicators 108 may receive one or more signals 110 associated with the frequency with which one or more sterilization agents 104 were applied to one or more objects 106. In some embodiments, one or more sterilization indicators 108 may receive one or more signals 110 associated with the intensity with which one or more sterilization agents 104 were applied to one or more objects 106. In some embodiments, one or more sterilization indicators 108 may receive one or more signals 110 which indicate that one or more objects 106 were sterilized in accordance with one or more protocols. In some embodiments, one or more sterilization indicators 108 may receive one or more signals 110 which indicate that one or more objects 106 have been sterilized in accordance with one or more protocols. In some embodiments, one or more sterilization indicators 108 may receive one or more signals 110 which indicate that one or more objects 106 have not been sterilized in accordance with one or more protocols. In some embodiments, one or more sterilization indicators 108 may receive one or more signals 110 which associate one or more sterilization statuses with one or more objects 106. In some embodiments, one or more sterilization indicators 108 may receive one or more signals 110 that change the sterilization status of the one or more sterilization indicators 108. In some embodiments, one or more sterilization indicators 108 may receive one or more signals 110 associated with one or more recording units 112. In some embodiments, one or more sterilization indicators 108 may receive one or more signals 110 associated with one or more controlling units 114.

The operational flow 500 also includes a reconfiguring operation 520 involving reconfiguring one or more sterilization indicators that are associated with one or more objects in accordance with the one or more signals. In some embodiments, one or more sterilization indicators 108 that are associated with one or more objects 106 may reconfigure in accordance with one or more signals 110. In some embodiments, one or more sterilization indicators 108 receive one or more signals 110 from one or more sterilization units 102. In some embodiments, one or more sterilization indicators 108 receive one or more signals 110 from one or more controlling units 114. In some embodiments, one or more sterilization indicators 108 receive one or more signals 110 from one or more recording units 112. In some embodiments, one or more sterilization indicators 108 receive one or more signals 110 from one or more user interactions 116.

In some embodiments, one or more sterilization indicators 108 are reconfigured to indicate that the one or more objects 106 with which they are associated are sterile. In some embodiments, one or more sterilization indicators 108 are reconfigured to indicate that the one or more objects 106 with which they are associated are not sterile. In some embodiments, one or more sterilization indicators 108 are reconfigured to indicate one or more sterilization statuses associated with one or more objects 106 to which the one or more sterilization indicators 108 are associated.

Figure 6:
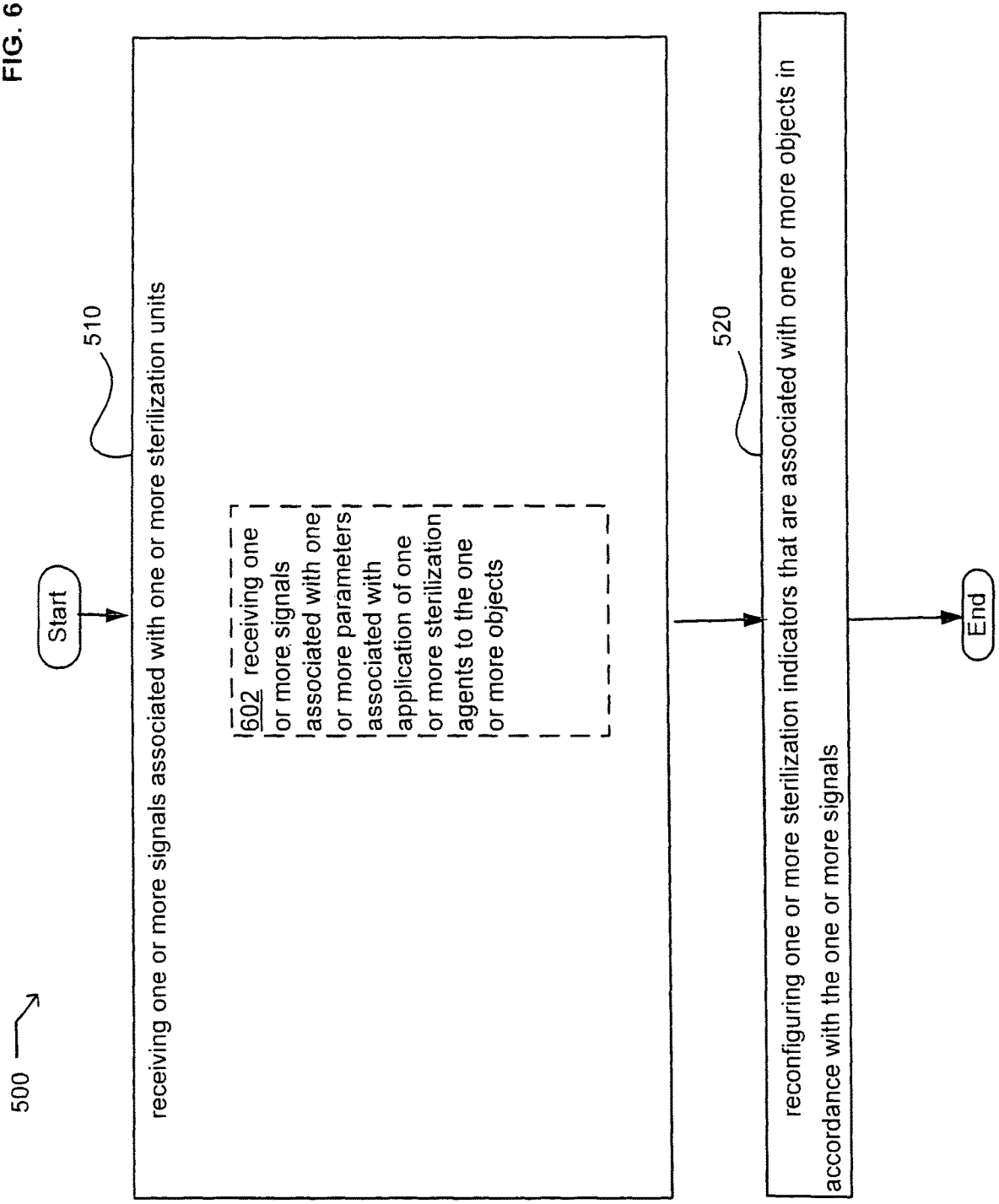
FIG. 6 illustrates an alternative embodiment of the example operation flow of FIG. 5.

FIG. 6 illustrates alternative embodiments of the example operational flow 500 of FIG. 5. FIG. 6 illustrates example embodiments where the receiving operation 510 may include at least one additional operation. Additional operations may include an operation 602.

At operation 602, the receiving operation 510 may include receiving one or more signals 110 associated with one or more parameters associated with application of one or more sterilization agents 104 to one or more objects 106. In some embodiments, one or more sterilization indicators 108 receive one or more signals 110 associated with one or more parameters associated with application of one or more sterilization agents 104 to one or more objects 106. Numerous parameters may be received. Examples of such parameters include, but are not limited to, one or more times of application, one or more intensities of application, one or more frequencies of application, one or more durations of application, one or more types of sterilization agents 104 used for application, one or more protocols used for application, and/or substantially any combination thereof that was used to sterilize one or more objects 106. In some embodiments, one or more sterilization indicators 108 receive one or more signals 110 instructing the one or more sterilization indicators 108 to indicate nonsterile status. In some embodiments, one or more sterilization indicators 108 receive one or more signals 110 instructing the one or more sterilization indicators 108 to indicate sterile status. In some embodiments, one or more sterilization indicators 108 receive one or more signals 110 instructing the one or more sterilization indicators 108 to indicate when one or more objects 106 should be sterilized.

Figure 7:
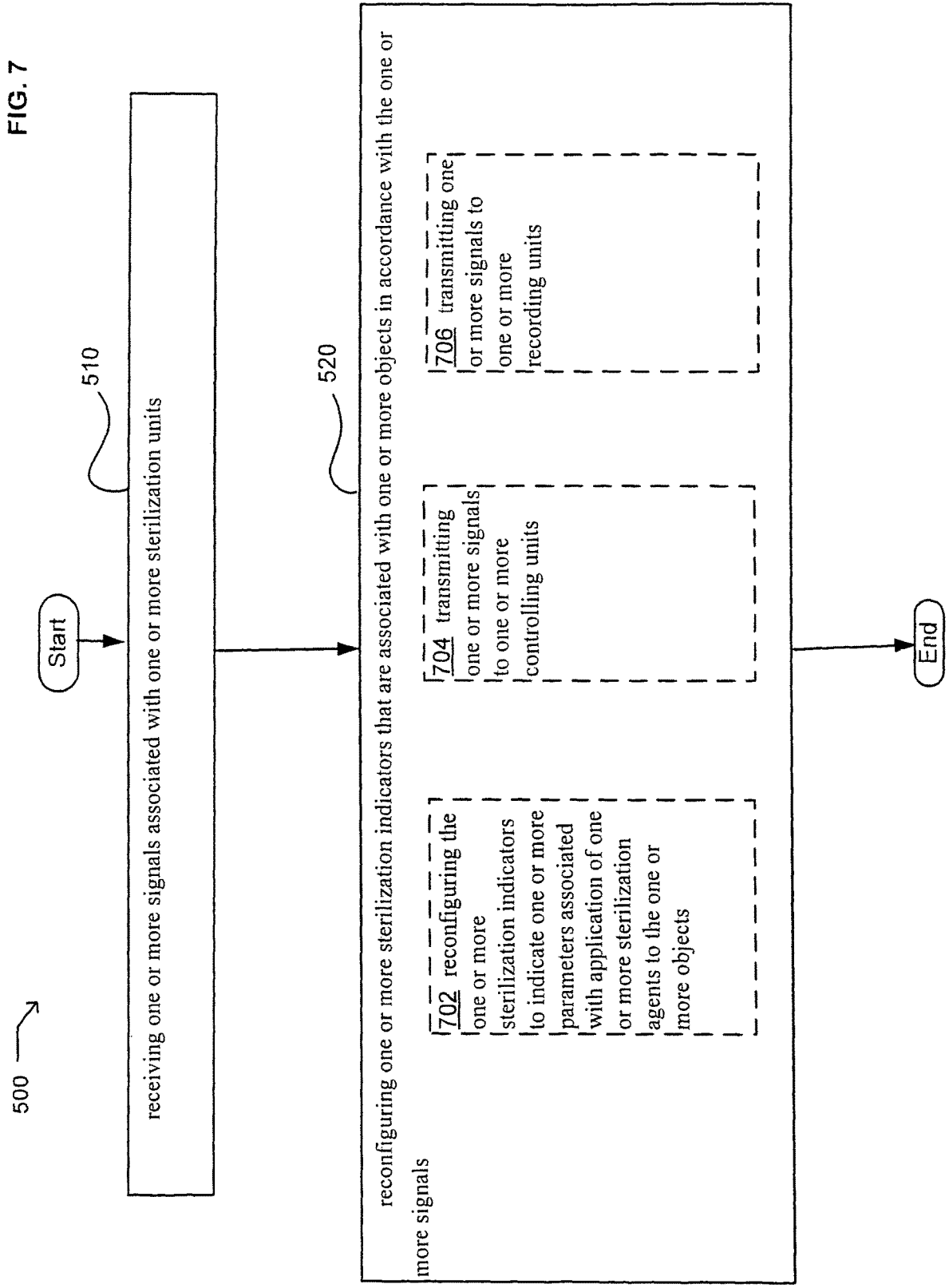
FIG. 7 illustrates an alternative embodiment of the example operation flow of FIG. 5.

FIG. 7 illustrates alternative embodiments of the example operational flow 500 of FIG. 5. FIG. 7 illustrates example embodiments where the reconfiguring operation 520 may include at least one additional operation. Additional operations may include an operation 702, operation 704 and/or operation 706.

At operation 702, the reconfiguring operation 520 may include reconfiguring the one or more sterilization indicators 108 to indicate one or more parameters associated with application of one or more sterilization agents 104 to the one or more objects 106.

In some embodiments, one or more sterilization indicators 108 are reconfigured to indicate one or more parameters associated with sterilization of one or more objects 106 with which the sterilization indicators 108 are associated. In some embodiments, one or more sterilization indicators 108 may be reconfigured with regard to one or more parameters associated with application of one or more sterilization agents 104 to one or more objects 106. Examples of such parameters include, but are not limited to, one or more times of application, one or more intensities of application, one or more frequencies of application, one or more durations of application, one or more types of sterilization agents 104 used for application, one or more protocols used for application, and/or substantially any combination thereof that was used to sterilize one or more objects 106. In some embodiments, one or more sterilization indicators 108 can be reconfigured to indicate nonsterile status. In some embodiments, one or more sterilization indicators 108 can be reconfigured to indicate sterile status. In some embodiments, one or more sterilization indicators 108 can be reconfigured to indicate when one or more objects 106 should be sterilized.

At operation 704, the reconfiguring operation 520 may include transmitting one or more signals 110 to one or more controlling units 114. In some embodiments, one or more sterilization indicators 108 may transmit one or more signals 110 associated with one or more controlling units 114. In some embodiments, one or more sterilization indicators 108 may transmit one or more signals 110 that instruct the one or more controlling units 114 to act. In some embodiments, one or more sterilization indicators 108 may transmit one or more signals 110 that instruct the one or more controlling units 114 not to act. In some embodiments, one or more sterilization indicators 108 may transmit one or more signals 110 instructing one or more controlling units 114 to allow one or more objects 106 associated with one or more sterilization indicators 108 to enter into one or more spaces. In some embodiments, one or more sterilization indicators 108 may transmit one or more signals 110 instructing one or more controlling units 114 to disallow one or more objects 106 associated with one or more sterilization indicators 108 from entering one or more spaces. In some embodiments, one or more sterilization indicators 108 may transmit one or more signals 110 instructing one or more controlling units 114 to allow one or more objects 106 associated with one or more sterilization indicators 108 to exit from one or more spaces. In some embodiments, one or more sterilization indicators 108 may transmit one or more signals 110 instructing one or more controlling units 114 to disallow one or more objects 106 associated with one or more sterilization indicators 108 from exiting one or more spaces. In some embodiments, one or more sterilization indicators 108 may transmit one or more signals 110 to one or more devices which include one or more controlling units 114 that control operation of the device.

At operation 706, the reconfiguring operation 520 may include transmitting one or more signals 110 to one or more recording units 112. In some embodiments, one or more sterilization indicators 110 may transmit one or more signals 110 associated with one or more recording units 112. In some embodiments, one or more sterilization indicators 108 may transmit one or more signals 110 to one or more recording units 112 indicating compliance of one or more objects 106 with a sterilization protocol. In some embodiments, one or more sterilization indicators 108 may transmit one or more signals 101 to one or more recording units 112 indicating noncompliance of one or more objects 106 with a sterilization protocol. In some embodiments, one or more sterilization indicators 110 may transmit one or more signals 110 to one or more recording units 112 indicating movement of one or more objects 106 about one or more spaces. In some embodiments, one or more sterilization indicators 108 may transmit one or more signals 110 to one or more recording units 112 indicating one or more parameters associated with one or more objects 106. Numerous parameters associated with one or more objects 106 may be transmitted. In some embodiments, one or more sterilization indicators 108 may transmit one or more signals 110 associated with parameters associated with application of one or more sterilization agents 104 to one or more objects 106. Examples of such parameters include, but are not limited to, one or more times of application, one or more intensities of application, one or more frequencies of application, one or more durations of application, one or more types of sterilization agents 104 used for application, one or more protocols used for application, and/or substantially any combination thereof that was used to sterilize one or more objects 106.

Figure 8:
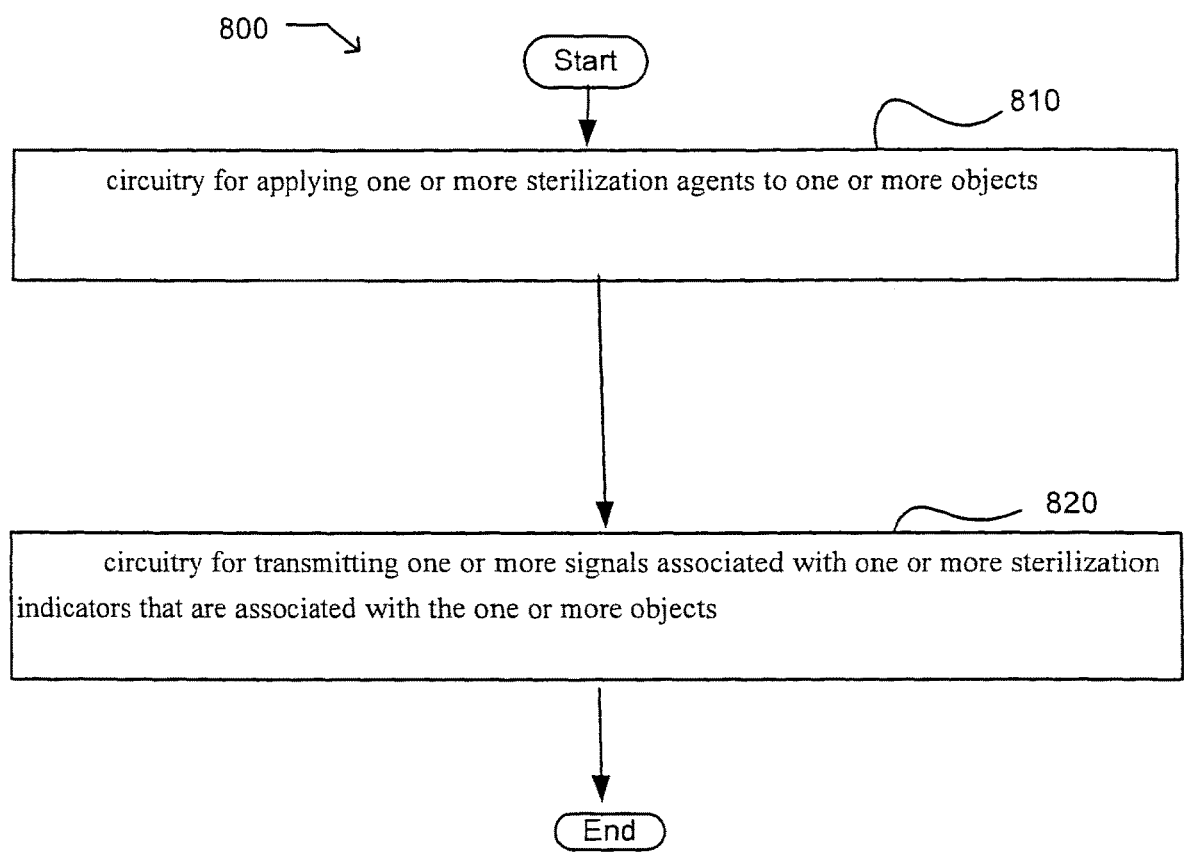
FIG. 8 illustrates an operational flow representing example operations related to sterilization methods.

FIG. 8 illustrates an operational flow 800 representing examples of operations that are related to the performance of a sterilization method. FIG. 8 illustrates various examples of operations used during performance of the sterilization method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 800 includes an operation 810 involving circuitry for applying one or more sterilization agents to one or more objects 106. In some embodiments, one or more sterilization units 102 include circuitry for applying one or more sterilization agents 104 to one or more objects 106. In some embodiments, the one or more sterilization units 102 may be mobile. For example, in some embodiments, the one or more sterilization units 102 may be positioned on a cart that may be transported throughout a facility such as a hospital, food processing facility, pharmaceutical manufacturing facility, dental office, and the like. In some embodiments, the one or more sterilization units 102 may be immobile. For example, in some embodiments, the one or more sterilization units 102 may be mounted on a wall of a hospital, food processing facility, pharmaceutical manufacturing facility, dental office, and the like.

In some embodiments, one or more sterilization units 102 include circuitry for applying one type of sterilization agent to one or more objects 106. In some embodiments, one or more sterilization units 102 include circuitry for applying one or more types of sterilization agents 104 to one or more objects 106. One or more sterilization units 102 may include circuitry for applying numerous types of sterilization agents 104 to one or more objects 106. Examples of such sterilization agents 104 include, but are not limited to, ultraviolet light, gamma radiation, sonic radiation, chemicals, infrared radiation, steam, gases, and the like. Numerous types of sterilization agents 104 are known and are commercially available.

In some embodiments, one or more sterilization units 102 may include circuitry for applying additional materials to one or more objects 106 that are not sterilizing agents. For example, in some embodiments, one or more sterilization units 102 may include circuitry for rinsing one or more objects 106 with water. In some embodiments, one or more sterilization units 102 may include circuitry for blowing air onto one or more objects 106 to dry the one or more objects 106. In some embodiments, one Or more sterilization units 102 may include circuitry for applying one or more sterilization indicators 108 to one or more objects 106 to indicate that the one or more objects 106 were sterilized. For example, in some embodiments, one or more sterilization units 102 may include circuitry for applying one or more sterilization indicators 108 that are dyes to one or more objects 106 following sterilization of the one or more objects 106.

One or more sterilization units 102 may include circuitry for applying one or more sterilization agents 104 to numerous types of objects 106. In some embodiments, the one or more objects 106 are medical instruments. In some embodiments, the one or more objects 106 are dental instruments. In some embodiments, the one or more objects 106 are humans. In some embodiments, the one or more objects 106 are portions of a human. For example, in some embodiments, the one or more objects 106 are human hands. Accordingly, the one or more sterilization units 102 may apply one or more sterilization agents 104 to one or more human hands.

The operational flow 800 also includes an operation 820 involving circuitry for transmitting one or more signals associated with one or more sterilization indicators that are associated with the one or more objects. In some embodiments, one or more sterilization units 102 include circuitry for transmitting one or more signals 110 associated with one or more sterilization indicators 108 that are associated with one or more objects 106. In some embodiments, one or more sterilization units 102 may include circuitry for transmitting one or more signals 110 to one or more sterilization indicators 108 that are physically coupled to one or more objects 106. In some embodiments, one or more sterilization units 102 may include circuitry for transmitting one or more signals 110 to one or more sterilization indicators 108 that are not physically coupled to one or more objects 106. In some embodiments, one or more sterilization units 102 may include circuitry for transmitting one or more signals 110 associated with the type or types of sterilization agents 104 that were applied to one or more objects 106. In some embodiments, one or more sterilization units 102 may include circuitry for transmitting one or more signals 110 associated with the frequency with which one or more sterilization agents 104 were applied to one or more objects 106. In some embodiments, one or more sterilization units 102 may include circuitry for transmitting one or more signals 110 associated with the intensity with which one or more sterilization agents 104 were applied to one or more objects 106. In some embodiments, one or more sterilization units 102 may include circuitry for transmitting one or more signals 110 which indicate that the one or more objects 106 were sterilized in accordance with one or more protocols. In some embodiments, one or more sterilization units 102 may include circuitry for transmitting one or more signals 110 which indicate that the one or more objects 106 have been sterilized in accordance with one or more protocols. In some embodiments, one or more sterilization units 102 may include circuitry for transmitting one or more signals 110 which indicate that the one or more objects 106 have not been sterilized in accordance with one or more protocols. In some embodiments, one or more sterilization units 102 may include circuitry for transmitting one or more signals 110 which associate one or more sterilization statuses with one or more objects 106. In some embodiments, one or more sterilization units 102 may include circuitry for transmitting one or more signals 110 that change the sterilization status of one or more sterilization indicators 108 that are associated with one or more objects 106. In some embodiments, one or more sterilization units 102 may include circuitry for transmitting one or more signals 110 associated with one or more recording units 112. In some embodiments, one or more sterilization units 102 may include circuitry for transmitting one or more signals 110 associated with one or more controlling units 114.

Figure 9:
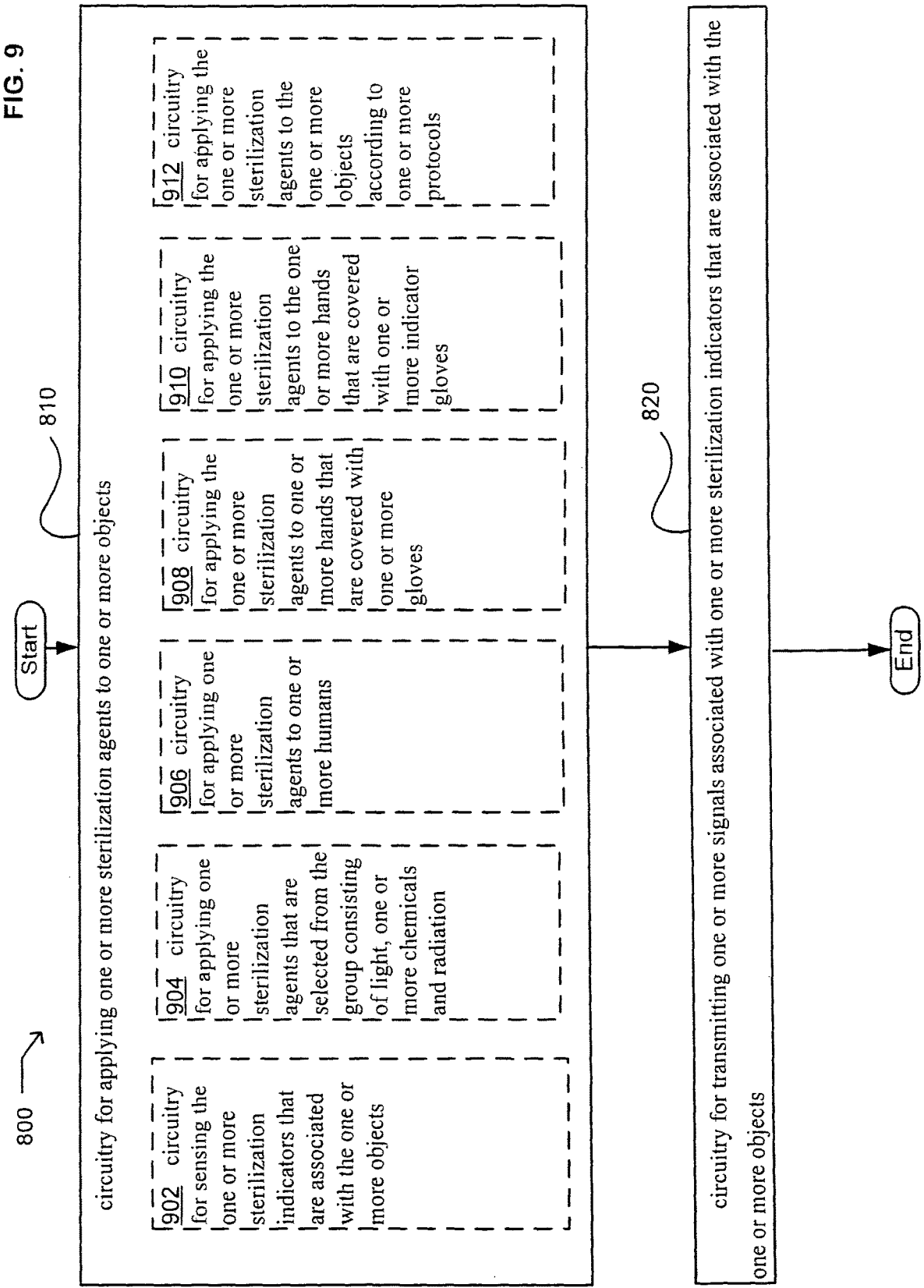
FIG. 9 illustrates an alternative embodiment of the example operation flow of FIG. 8.

FIG. 9 illustrates alternative embodiments of the example operational flow 800 of FIG. 8. FIG. 9 illustrates example embodiments where the circuitry for applying operation 810 may include at least one additional operation. Additional operations may include an operation 902, operation 904, operation 906, operation 908, operation 910 and/or operation 912.

At operation 902, the circuitry for applying operation 810 may include circuitry for sensing one or more sterilization indicators 108 that are associated with one or more objects 106. In some embodiments, one or more sterilization units 102 may include circuitry for sensing one or more sterilization indicators 108 that are associated with one or more objects 106. In some embodiments, one or more sterilization units 102 may include circuitry for sensing the presence of one or more sterilization indicators 108 that are associated with one or more objects 106. In some embodiments, one or more sterilization units 102 may include circuitry for sensing the absence of one or more sterilization indicators 108 that are associated with one or more objects 106. In some embodiments, one or more sterilization units 102 may include circuitry for determining what type or types of sterilization agents 104 to apply to one or more objects 106. In some embodiments, one or more sterilization units 102 may include circuitry for determining what type or types of sterilization agents 104 not to apply to one or more objects 106. In some embodiments, one or more sterilization units 102 may include circuitry for determining whether to apply one or more sterilization agents 104 to one or more objects 106 in accordance with a sterilization protocol. In some embodiments, one or more sterilization units 102 may include circuitry for determining the intensity with which to apply one or more sterilization agents 104 to one or more objects 106. In some embodiments, one or more sterilization units 102 may include circuitry for determining the frequency with which to apply one or more sterilization agents 104 to one or more objects 106. In some embodiments, one or more sterilization units 102 may include circuitry for determining when one or more sterilization agents 104 were last applied to one or more objects 106. In some embodiments, one or more sterilization units 102 may include circuitry for determining when one or more sterilization agents 104 should be applied to one or more objects 106.

At operation 904, the circuitry for applying operation 810 may include circuitry for applying one or more sterilization agents 104 that are selected from the group consisting of light, one or more chemicals and radiation. In some embodiments, one or more sterilization units 102 include circuitry for applying one or more sterilization agents 104 that are selected from the group consisting of light, one or more chemicals and radiation. In some embodiments, one or more sterilization units 102 may include circuitry for applying one or more sterilization agents 104 that include light. In some embodiments, one or more sterilization units 102 include circuitry for applying sterilizing light. In some embodiments, one or more sterilization units 102 may include circuitry for applying ultraviolet light. In some embodiments, one or more sterilization units 102 may include circuitry for applying nonsterilizing light. For example, in some embodiments, visible light may be applied to one or more objects 106. In some embodiments, one or more sterilization units 102 include circuitry for applying one or more sterilization agents 104 that include one or more chemicals. Numerous types of chemicals may be applied by one or more sterilization units 102. In some embodiments, one or more chemicals may be applied that do not sterilize one or more objects 106. For example, in some embodiments, one or more chemicals that are sterilization indicators 108 may be applied to one or more objects 106. In some embodiments, one or more chemicals may be applied to one or more objects 106 that wash the one or more objects 106 without sterilizing the one or more objects 106. In some embodiments, one or more chemicals may be applied that sterilize one or more objects 106. Examples of such chemicals include, but are not limited to, alcohol, chlorine, ammonia, ozone, ethylene oxide, peroxides, acids, bases, and the like. In some embodiments, one or more sterilization units 102 include circuitry for applying one or more sterilization agents 104 that include one or more types of radiation. Examples of types of radiation include, but are not limited to, gamma radiation, infrared radiation, beta radiation, and the like. In some embodiments, one or more sterilization units 102 may include circuitry for applying one type of sterilization agent to one or more objects 106. In some embodiments, one or more sterilization units 102 may include circuitry for applying one or more types of sterilization agents 104 to one or more objects 106.

At operation 906, the circuitry for applying operation 810 may include circuitry for applying one or more sterilization agents 104 to one or more humans. In some embodiments, one or more sterilization units 102 may include circuitry for applying one or more sterilization agents 104 to one or more humans. In some embodiments, one or more sterilization units 102 may include circuitry for applying one or more sterilization agents 104 to all accessible surfaces of one or more humans. For example, in some embodiments, one or more sterilization units 102 may be configured as a shower where one or more sterilization agents 104 may be applied to one or more humans. In some embodiments, the one or more humans may be covered with clothing or other protective wear. In some embodiments, the one or more humans may not be covered with clothing or other protective wear. In some embodiments, one or more sterilization units 102 may include circuitry for applying one or more sterilization agents 104 to one or more portions of a human. For example, in some embodiments, one or more sterilization units 102 are configured to apply one or more sterilization agents 104 to one or more feet. In some embodiments, one or more sterilization units 102 are configured to apply one or more sterilization agents 104 to one or more hands. In some embodiments, one or more sterilization units 102 are configured to apply one or more sterilization agents 104 to one or more arms and hands. In some embodiments, the one or more portions of one or more humans may be covered with clothing or other protective wear. In some embodiments, the one or more portions of one or more humans may not be covered with clothing or other protective wear.

At operation 908, the circuitry, for applying operation 810 may include circuitry for applying the one or more sterilization agents 104 to one or more hands that are covered with one or more gloves. In some embodiments, one or more sterilization units 102 may include circuitry for applying one or more sterilization agents 104 to one or more hands that are covered with one or more gloves. In some embodiments, one or more sterilization units 102 are configured as hand sterilizers to apply one or more sterilization agents 104 onto one or more hands. In some embodiments, one or more sterilization units 102 include circuitry for applying one or more gloves to one or more hands. For example, in some embodiments, one or more hands may be placed within one or more sterilization units 102 where gloves may be applied to the one or more hands by the one or more sterilization units 102. In some embodiments, rubber gloves may be stretched over one or more hands that are placed within one or more sterilization units 102. In other embodiments, one or more gloves may be formed on one or more hands through application of one or more coat forming compounds to the one or more hands. For example, in some embodiments, non-toxic paint may be sprayed onto one or more hands to form one or more gloves. In some embodiments, one or more coat forming compounds may be applied to one or more hands that are covered with gloves. For example, one or more hands may each be covered with a latex glove to which one or more coat forming compounds are applied. In some embodiments, metalized gloves are used to cover one or more hands. Numerous examples of metalized gloves are known and are commercially available (i.e., Newtex Industries, Inc., Victor, N.Y.). In some embodiments, one or more hands may be covered with one or more gloves that protect the one or more hands from one or more sterilization agents 104 that are applied to the one or more hands.

At operation 910, the circuitry for applying operation 810 may include circuitry for applying one or more sterilization agents 104 to one or more hands that are covered with one or more indicator gloves. In some embodiments, one or more sterilization units 102 may include circuitry for applying one or more sterilization agents 104 to one or more hands that are covered with one or more indicator gloves. In some embodiments, one or more indicator gloves indicate if one or more sterilization agents 104 were applied to the one or more indicator gloves. In some embodiments, one or more indicator gloves indicate when one or more sterilization agents 104 were applied to the one or more indicator gloves. In some embodiments, one or more indicator gloves indicate what type or types of sterilization agents 104 were applied to the one or more indicator gloves. In some embodiments, one or more indicator gloves indicate if one or more sterilization agents 104 should be applied to the one or more indicator gloves. Numerous technologies may be used to produce indicator gloves. In some embodiments, a phosphorescent dye may be included within the indicator gloves that will emit light upon being exposed to ultraviolet light. Accordingly, in some embodiments, such indicator gloves may be used to indicate the intensity with which the indicator gloves were irradiated with ultraviolet light. In some embodiments, such indicator gloves may be used to indicate when the indicator gloves were last irradiated with ultraviolet light. In some embodiments, indicator gloves may include one or more chemicals that change color upon being sterilized. Such chemicals are known and are commercially available (i.e., JP Laboratories, Inc., Middlesex, N.J.). In some embodiments, one or more indicator gloves may include one or more sterilization indicators 108.

At operation 912, the circuitry for applying operation 810 may include circuitry for applying one or more sterilization agents 104 to one or more objects 106 according to one or more protocols. In some embodiments, one or more sterilization units 102 may include circuitry for applying one or more sterilization agents 104 to one or more objects 106 according to one or more protocols. In some embodiments, one or more sterilization protocols may be associated with one or more objects 106. In some embodiments, a sterilization protocol may specify the immediacy, latency, intensity and time-integrated intensity of sterilizing radiation that is to be applied to one or more objects 106. In some embodiments, a sterilization protocol may specify one or more types of sterilization agents 104 that are to be applied to one or more objects 106. In some embodiments, a sterilization protocol may specific one or more types of sterilization agents 104 that are not to be applied to one or more objects 106. In some embodiments, a sterilization protocol may specify the frequency with which one or more sterilization agents 104 are to be applied to one or more objects 106. In some embodiments, a sterilization protocol may specify the intensity and/or concentration that one or more types of sterilization agents 104 are to be applied to one or more objects 106. Numerous sterilization protocols can be assigned to one or more objects 106. In some embodiments, such protocols can be used to specify the intensity with which one or more objects 106 are sterilized to account for high patient-hazard and/or high infectivity use of the one or more objects 106 to ensure that such objects 106 receive rigorous and/or frequent sterilization treatment. Accordingly, in some embodiments, one or more sterilization indicators 108 can include circuitry for communicating with one or more sterilization units 102 to determine if one or more objects 106 have been sterilized in accordance with a sterilization protocol. In some embodiments, one or more sterilization indicators 108 can include circuitry for indicating how much time has passed since one or more objects 106 were last sterilized. In some embodiments, one or more sterilization indicators 108 can include circuitry for communicating with one or more sterilization units 102 to indicate when one or more objects 106 were last sterilized. In some embodiments, one or more sterilization indicators 108 can include circuitry for communicating with one or more recording units 112 to indicate when one or more objects 106 were last sterilized. In some embodiments, one or more sterilization indicators 108 can include circuitry for communicating with one or more sterilization units to determine when one or more objects 106 were last sterilized.

Figure 10:
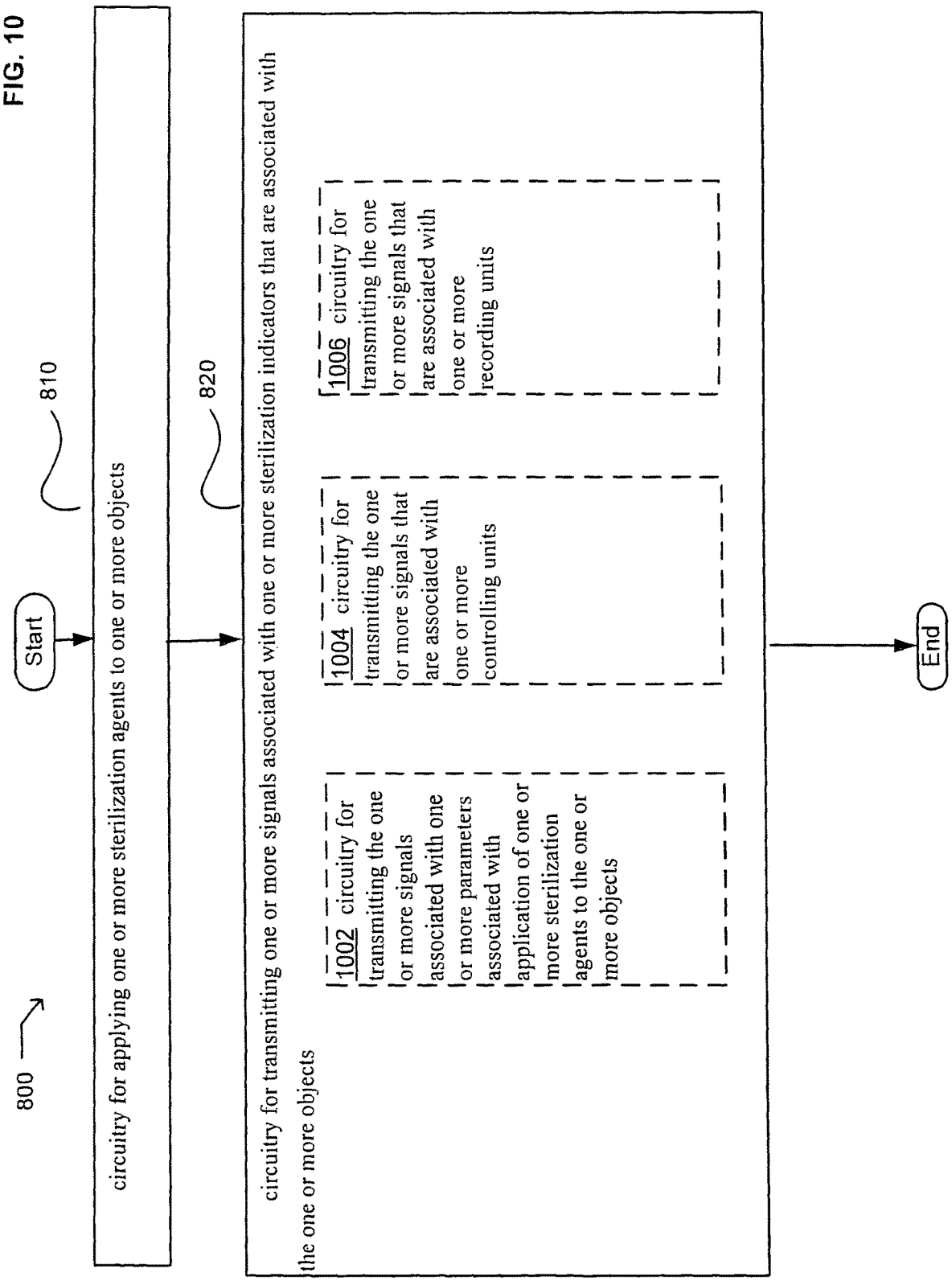
FIG. 10 illustrates an alternative embodiment of the example operation flow of FIG. 8.

FIG. 10 illustrates alternative embodiments of the example operational flow 800 of FIG. 8. FIG. 10 illustrates example embodiments where the circuitry for transmitting operation 820 may include at least one additional operation. Additional operations may include an operation 1002, operation 1004 and/or operation 1006.

At operation 1002, the transmitting operation 820 may include circuitry for transmitting one or more signals 110 associated with one or more parameters associated with application of one or more sterilization agents 104 to one or more objects 106. In some embodiments, one or more sterilization units 102 may include circuitry for transmitting one or more signals 110 associated with one or more parameters associated with application of one or more sterilization agents 104 to one or more objects 106. In some embodiments, one or more sterilization units 102 may include circuitry for transmitting one or more signals 110 associated with one or more times of application, one or more intensities of application, one or more frequencies of application, one or more durations of application, one or more types of sterilization agents 104 used for application, one or more protocols used for application, and/or substantially any combination thereof that was used to sterilize one or more objects 106.

At operation 1004, the transmitting operation 820 may include circuitry for transmitting one or more signals 110 that are associated with one or more controlling units 114. In some embodiments, one or more sterilization units 102 may include circuitry for transmitting one or more signals 110 associated with one or more controlling units 114. In some embodiments, one or more sterilization units 102 may include circuitry for transmitting one or more signals 110 that instruct the one or more controlling units 114 to act. In some embodiments, one or more sterilization units 102 may include circuitry for transmitting one or more signals 110 that instruct the one or more controlling units 114 not to act. In some embodiments, one or more sterilization units 102 may include circuitry for transmitting one or more signals 110 instructing one or more controlling units 114 to allow one or more objects 106 associated with one or more sterilization indicators 108 to enter into one or more spaces. In some embodiments, one or more sterilization units 102 may include circuitry for transmitting one or more signals 110 instructing one or more controlling units 114 to disallow one or more objects 106 associated with one or more sterilization indicators 108 from entering one or more spaces. In some embodiments, one or more sterilization units 102 may include circuitry for transmitting one or more signals 110 instructing one or more controlling units 114 to allow one or more objects 106 associated with one or more sterilization indicators 108 to exit from one or more spaces. In some embodiments, one or more sterilization units 102 may include circuitry for transmitting one or more signals 110 instructing one or more controlling units 114 to disallow one or more objects 106 associated with one or more sterilization indicators 108 from exiting one or more spaces. In some embodiments, one or more sterilization units 102 may include circuitry for transmitting one or more signals 110 to one or more devices which include one or more controlling units 114 that control operation of the device.

At operation 1006, the transmitting operation 820 may include circuitry for transmitting one or more signals 110 that are associated with one or more recording units 112. In some embodiments, one or more sterilization units 102 may include circuitry for transmitting one or more signals 110 associated with one or more recording units 112. In some embodiments, one or more sterilization units 102 may include circuitry for transmitting one or more signals 110 to one or more recording units 112 indicating compliance of one or more objects 106 with a sterilization protocol. In some embodiments, one or more sterilization units 102 may include circuitry for transmitting one or more signals 110 to one or more recording units 112 indicating noncompliance of one or more objects 106 with a sterilization protocol. In some embodiments, one or more sterilization units 102 may include circuitry for transmitting one or more signals 110 to one or more recording units 112 indicating movement of one or more objects 106 about one or more spaces. In some embodiments, one or more sterilization units 102 may include circuitry for transmitting one or more signals 110 to one or more recording units 112 indicating one or more parameters associated with one or more objects 106. Numerous parameters associated with one or more objects 106 may be transmitted. In some embodiments, one or more sterilization units 102 may include circuitry for transmitting one or more signals 110 associated with parameters associated with application of one or more sterilization agents 104 to one or more objects 106. Examples of such parameters include, but are not limited to, one or more times of application, one or more intensities of application, one or more frequencies of application, one or more durations of application, one or more types of sterilization agents 104 used for application, one or more protocols used for application, and/or substantially any combination thereof that was used to sterilize one or more objects 106.

Figure 11:
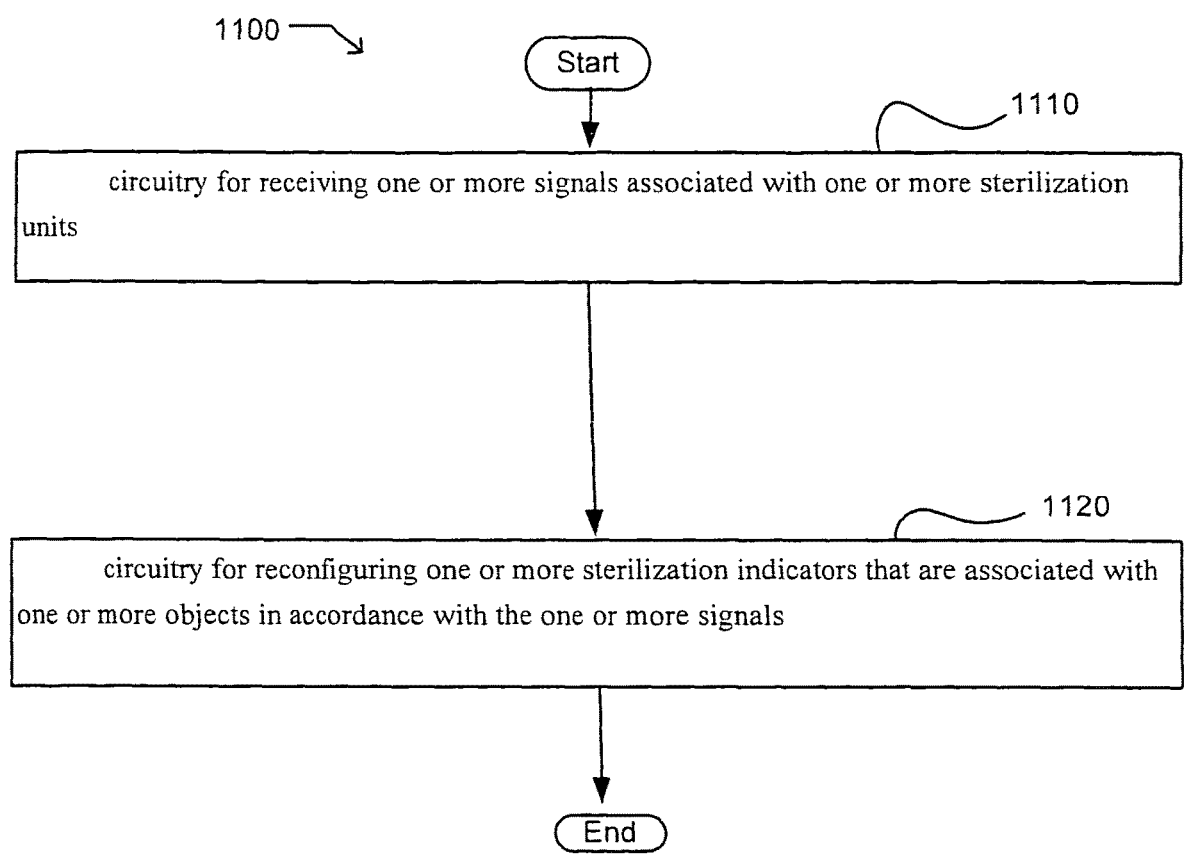
FIG. 11 illustrates an operational flow representing example operations related to sterilization methods.

FIG. 11 illustrates an operational flow 1100 representing examples of operations that are related to the performance of a sterilization method. FIG. 11 illustrates various examples of operations used during performance of the sterilization method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 1100 includes an operation 1110 involving circuitry for receiving one or more signals associated with one or more sterilization units. In some embodiments, one or more sterilization indicators 108 may include circuitry for receiving one or more signals 110 associated with one or more sterilization units 102. In some embodiments, the one or more sterilization indicators 108 are physically coupled to one or more objects 106. In some embodiments, the one or more sterilization indicators 108 are not physically coupled to one or more objects 106. In some embodiments, one or more sterilization indicators 108 may include circuitry for receiving one or more signals 110 associated with the type or types of sterilization agents 104 that were applied to one or more objects 106. In some embodiments, one or more sterilization indicators 108 may include circuitry for receiving one or more signals 110 associated with the frequency with which one or more sterilization agents 104 were applied to one or more objects 106. In some embodiments, one or more sterilization indicators 108 may include circuitry for receiving one or more signals 110 associated with the intensity with which one or more sterilization agents 104 were applied to one or more objects 106. In some embodiments, one or more sterilization indicators 108 may include circuitry for receiving one or more signals 110 which indicate that one or more objects 106 were sterilized in accordance with one or more protocols. In some embodiments, one or more sterilization indicators 108 may include circuitry for receiving one or more signals 110 which indicate that one or more objects 106 have been sterilized in accordance with one or more protocols. In some embodiments, one or more sterilization indicators 108 may include circuitry for receiving one or more signals 110 which indicate that one or more objects 106 have not been sterilized in accordance with one or more protocols. In some embodiments, one or more sterilization indicators 108 may include circuitry for receiving one or more signals 110 which associate one or more sterilization statuses with one or more objects 106. In some embodiments, one or more sterilization indicators 108 may include circuitry for receiving one or more signals 110 that change the sterilization status of the one or more sterilization indicators 108. In some embodiments, one or more sterilization indicators 108 may include circuitry for receiving one or more signals 110 associated with one or more recording units 112. In some embodiments, one or more sterilization indicators 108 may include circuitry for receiving one or more signals 110 associated with one or more controlling units 114.

The operational flow 1100 also includes an operation 1120 involving circuitry for reconfiguring one or more sterilization indicators that are associated with one or more objects in accordance with the one or more signals. In some embodiments, one or more sterilization indicators 108 that are associated with one or more objects 106 may include circuitry for reconfiguring one or more sterilization indicators 108 in accordance with one or more signals 110. In some embodiments, one or more sterilization indicators 108 may receive one or more signals 110 from one or more sterilization units 102. In some embodiments, one or more sterilization indicators 108 may receive one or more signals 110 from one or more controlling units 114. In some embodiments, one or more sterilization indicators 108 may receive one or more signals 110 from one or more recording units 112. In some embodiments, one or more sterilization indicators 108 may receive one or more signals 110 from one or more user interactions 116. In some embodiments, one or more sterilization indicators 108 include circuitry for reconfiguring the one or more sterilization indicators 108 to indicate that the one or more objects 106 with which they are associated are sterile. In some embodiments, one or more sterilization indicators 108 include circuitry for reconfiguring the one or more sterilization indicators 108 to indicate that the one or more objects 106 with which they are associated are not sterile. In some embodiments, one or more sterilization indicators 108 include circuitry for reconfiguring one or more sterilization indicators 108 to indicate one or more sterilization statuses associated with one or more objects 106 to which the one or more sterilization indicators 108 are associated.

Figure 12:
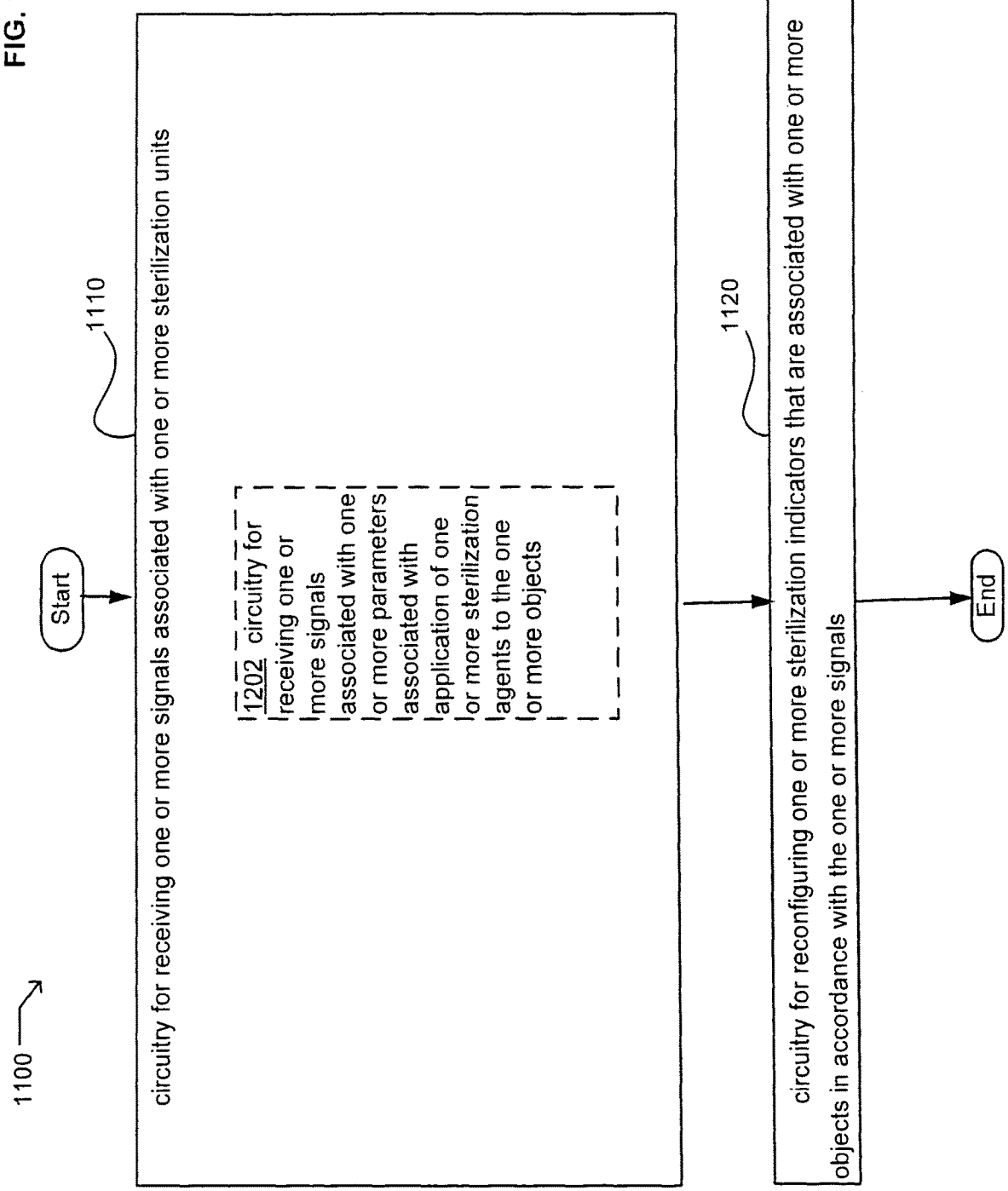
FIG. 12 illustrates an alternative embodiment of the example operation flow of FIG. 11.

FIG. 12 illustrates alternative embodiments of the example operational flow 1100 of FIG. 11. FIG. 12 illustrates example embodiments where the circuitry for receiving operation 1110 may include at least one additional operation. Additional operations may include an operation 1202.

At operation 1202, the circuitry for receiving operation 1110 may include circuitry for receiving one or more signals 110 associated with one or more parameters associated with application of one or more sterilization agents 104 to one or more objects 106. In some embodiments, one or more sterilization indicators 108 may include circuitry for receiving one or more signals 110 associated with one or more parameters associated with application of one or more sterilization agents 104 to one or more objects 106. Numerous parameters may be received. Examples of such parameters include, but are not limited to, one or more times of application, one or more intensities of application, one or more frequencies of application, one or more durations of application, one or more types of sterilization agents 104 used for application, one or more protocols used for application, and/or substantially any combination thereof that was used to sterilize one or more objects 106. In some embodiments, one or more sterilization indicators 108 may include circuitry for receiving one or more signals 110 instructing the one or more sterilization indicators 108 to indicate nonsterile status. In some embodiments, one or more sterilization indicators 108 may include circuitry for receiving one or more signals 110 instructing the one or more sterilization indicators 108 to indicate sterile status. In some embodiments, one or more sterilization indicators 108 may include circuitry for receiving one or more signals 110 instructing the one or more sterilization indicators 108 to indicate when one or more objects 106 should be sterilized.

Figure 13:
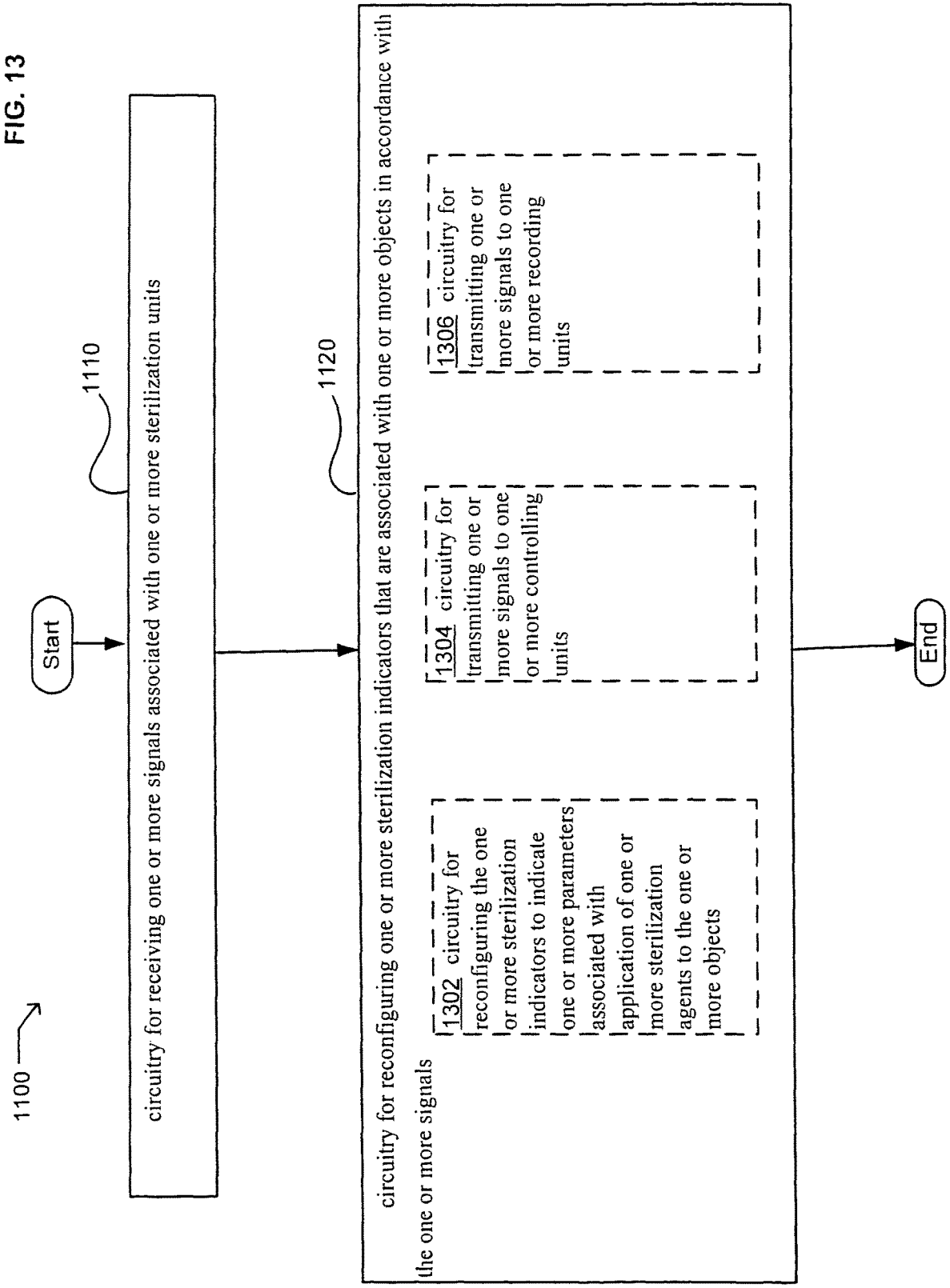
FIG. 13 illustrates an alternative embodiment of the example operation flow of FIG. 11.

FIG. 13 illustrates alternative embodiments of the example operational flow 1100 of FIG. 11. FIG. 13 illustrates example embodiments where the circuitry for reconfiguring 1120 may include at least one additional operation. Additional operations may include an operation 1302, operation 1304 and/or operation 1306.

At operation 1302, the circuitry for reconfiguring operation 1120 may include circuitry for reconfiguring one or more sterilization indicators 108 to indicate one or more parameters associated with application of one or more sterilization agents 104 to one or more objects 106. In some embodiments, one or more sterilization indicators 108 may include circuitry for reconfiguring one or more sterilization indicators 108 to indicate one or more parameters associated with application of one or more sterilization agents 104 to one or more objects 106. In some embodiments, one or more sterilization indicators 108 may include circuitry for reconfiguring one or more sterilization indicators 108 with regard to one or more parameters associated with application of one or more sterilization agents 104 to one or more objects 106. Examples of such parameters include, but are not limited to, one or more times of application, one or more intensities of application, one or more frequencies of application, one or more durations of application, one or more types of sterilization agents 104 used for application, one or more protocols used for application, and/or substantially any combination thereof that was used to sterilize one or more objects 106. In some embodiments, one or more sterilization indicators 108 may include circuitry for reconfiguring one or more sterilization indicators 108 to indicate nonsterile status. In some embodiments, one or more sterilization indicators 108 may include circuitry for reconfiguring one or more sterilization indicators 108 to indicate sterile status. In some embodiments, one or more sterilization indicators 108 may include-circuitry for reconfiguring one or more sterilization indicators 108 to indicate when one or more objects 106 should be sterilized.

At operation 1304, the circuitry for reconfiguring operation 1120 may include circuitry for transmitting one or more signals 110 to one or more controlling units 114. In some embodiments, one or more sterilization indicators 108 may include circuitry for transmitting one or more signals 110 associated with one or more controlling units 114. In some embodiments, one or more sterilization indicators 108 may include circuitry for transmitting one or more signals 110 that instruct the one or more controlling units 114 to act. In some embodiments, one or more sterilization indicators 108 may include circuitry for transmitting one or more signals 110 that instruct the one or more controlling units 114 not to act. In some embodiments, one or more sterilization indicators 108 may include circuitry for transmitting one or more signals 110 instructing one or more controlling units 114 to allow one or more objects 106 associated with one or more sterilization indicators 108 to enter into one or more spaces. In some embodiments, one or more sterilization indicators 108 may include circuitry for transmitting one or more signals 110 instructing one or more controlling units 114 to disallow one or more objects 106 associated with one or more sterilization indicators 108 from entering one or more spaces. In some embodiments, one or more sterilization indicators 108 may include circuitry for transmitting one or more signals 110 instructing one or more controlling units 114 to allow one or more objects 106 associated with one or more sterilization indicators 108 to exit from one or more spaces. In some embodiments, one or more sterilization indicators 108 may include circuitry for transmitting one or more signals 110 instructing one or more controlling units 114 to disallow one or more objects 106 associated with one or more sterilization indicators 108 from exiting one or more spaces. In some embodiments, one or more sterilization indicators 108 may include circuitry for transmitting one or more signals 110 to one or more devices which include one or more controlling units 114 that control operation of the device.

At operation 1306, the circuitry for reconfiguring operation 1120 may include circuitry for transmitting one or more signals 110 to one or more recording units 112. In some embodiments, one or more sterilization indicators 108 may include circuitry for transmitting one or more signals 110 associated with one or more recording units 112. In some embodiments, one or more sterilization indicators 108 may include circuitry for transmitting one or more signals 110 to one or more recording units 112 indicating compliance of one or more objects 106 with a sterilization protocol. In some embodiments, one or more sterilization indicators 110 may include circuitry for transmitting one or more signals 110 to one or more recording units 112 indicating noncompliance of one or more objects 106 with a sterilization protocol. In some embodiments, one or more sterilization indicators 108 may include circuitry for transmitting one or more signals 110 to one or more recording units 112 indicating movement of one or more objects 106 about one or more spaces. In some embodiments, one or more sterilization indicators 108 may include circuitry for transmitting one or more signals 110 to one or more recording units 112 indicating one or more parameters associated with one or more objects 106. Numerous parameters associated with one or more objects 106 may be transmitted. In some embodiments, one or more sterilization indicators 110 may include circuitry for transmitting one or more signals 110 associated with parameters associated with application of one or more sterilization agents 104 to one or more objects 106. Examples of such parameters include, but are not limited to, one or more times of application, one or more intensities of application, one or more frequencies of application, one or more durations of application, one or more types of sterilization agents 104 used for application, one or more protocols used for application, and/or substantially any combination thereof that was used to sterilize one or more objects 106.

Figure 14:
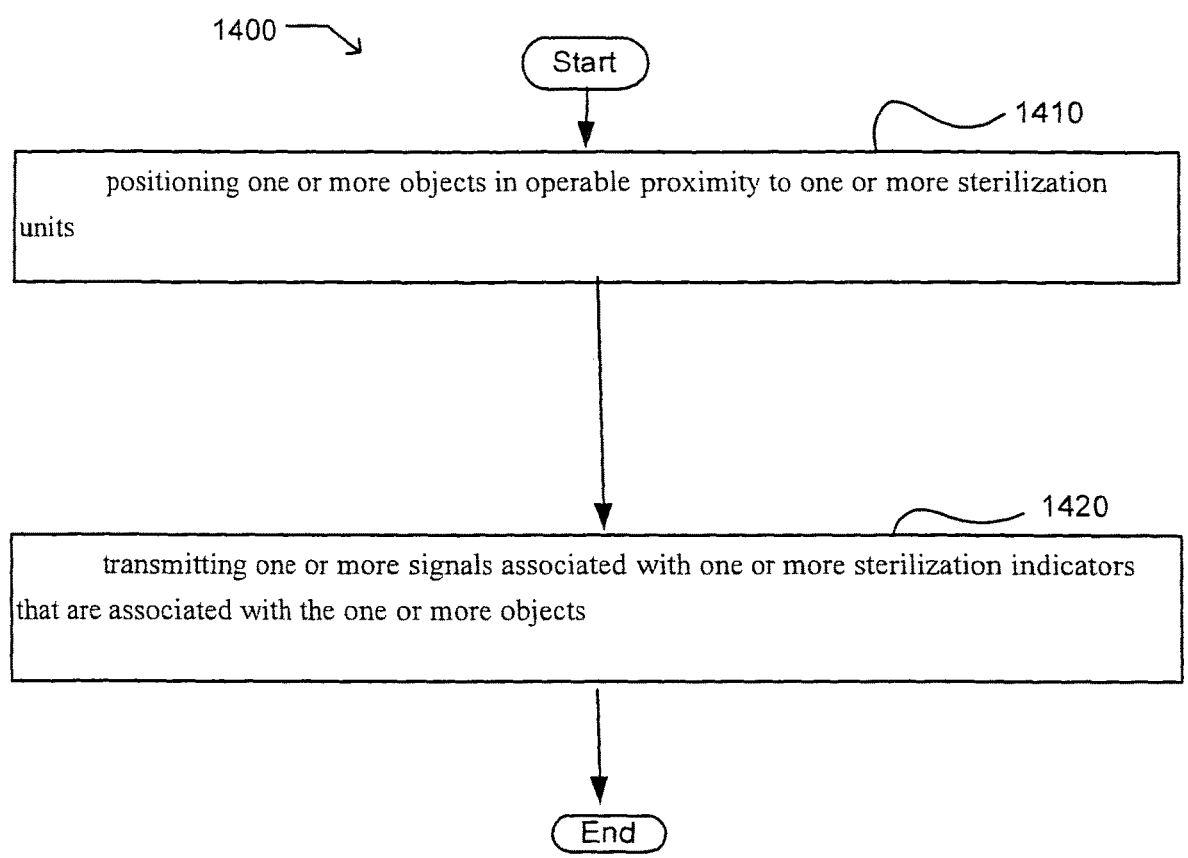
FIG. 14 illustrates an operational flow representing example operations related to sterilization methods.

FIG. 14 illustrates an operational flow 1400 representing examples of operations that are related to the performance of a sterilization method. FIG. 14 illustrates various examples of operations used during performance of the sterilization method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 1400 includes a positioning operation 1410 involving positioning one or more objects in operable proximity to one or more sterilization units. In some embodiments, one or more users 118 position one or more objects 106 in operable proximity to one or more sterilization units 102. In such embodiments, one or more sterilization units 102 can apply one or more sterilization agents 104 to the one or more objects 106. In some embodiments, one or more users 118 place one or more objects 106 within one or more sterilization units 102. In some embodiments, one or more users 118 place one or more of their hands within one or more sterilization units 102. In some embodiments, one or more users 118 place one or more of their arms and hands within one or more sterilization units 102. In some embodiments, one or more users 118 place one or more of their feet within one or more sterilization units 102. Numerous objects 106 may be positioned in operable proximity to one or more sterilization units 102. Examples of such objects 106 include, but are not limited to, humans, non-human animals, plants, medical instruments, cooking utensils, food storage devices, pharmaceutical formulation devices, food packaging devices, food preparation devices, eating utensils, dental instruments, and the like.

The operational flow 1400 also includes a transmitting operation 1420 involving transmitting one or more signals associated with one or more sterilization indicators that are associated with the one or more objects. In some embodiments, one or more sterilization indicators 108 may transmit one or more signals 110 associated with one or more parameters associated with application of one or more sterilization agents 104 to one or more objects 106. In some embodiments, one or more sterilization indicators 108 may transmit one or more signals 110 associated with one or more times of application, one or more intensities of application, one or more frequencies of application, one or more durations of application, one or more types of sterilization agents 104 used for application, one or more protocols used for application, and/or substantially any combination thereof that is to be used to sterilize one or more objects 106. In some embodiments, one or more sterilization indicators 108 may transmit one or more signals 110 associated with one or more controlling units 114. In some embodiments, one or more sterilization indicators 108 may transmit one or more signals 110 that instruct the one or more controlling units 114 to act. In some embodiments, one or more sterilization indicators 108 may transmit one or more signals 110 that instruct the one or more controlling units 114 not to act. In some embodiments, one or more sterilization indicators 108 may transmit one or more signals 110 instructing one or more controlling units 114 to allow one or more objects 106 associated with the one or more sterilization indicators 108 to enter into one or more spaces. In some embodiments, one or more sterilization indicators 108 may transmit one or more signals 110 instructing one or more controlling units 114 to disallow one or more objects 106 associated with the one or more sterilization indicators 108 from entering one or more spaces. In some embodiments, one or more sterilization indicators 108 may transmit one or more signals 110 instructing one or more controlling units 114 to allow one or more objects 106 associated with the one or more sterilization indicators 108 to exit from one or more spaces. In some embodiments, one or more sterilization indicators 108 may transmit one or more signals 110 instructing one or more controlling units 114 to disallow one or more objects 106 associated with the one or more sterilization indicators 108 from exiting one or more spaces. In some embodiments, one or more sterilization indicators 108 may transmit one or more signals 110 to one or more devices which include one or more controlling units 114 that control operation of the device. In some embodiments, one or more sterilization indicators 108 may transmit one or more signals 110 associated with one or more recording units 112. In some embodiments, one or more sterilization indicators 108 may transmit one or more signals 110 to one or more recording units 112 indicating compliance of one or more objects 106 with a sterilization protocol. In some embodiments, one or more sterilization indicators 108 may transmit one or more signals 110 to one or more recording units 112 indicating noncompliance of one or more objects 106 with a sterilization protocol. In some embodiments, one or more sterilization indicators 108 may transmit one or more signals 110 to one or more recording units 112 indicating movement of one or more objects 106 about one or more spaces. In some embodiments, one or more sterilization indicators 108 may transmit one or more signals 110 to one or more recording units 112 indicating one or more parameters associated with one or more objects 106.

Figure 15:
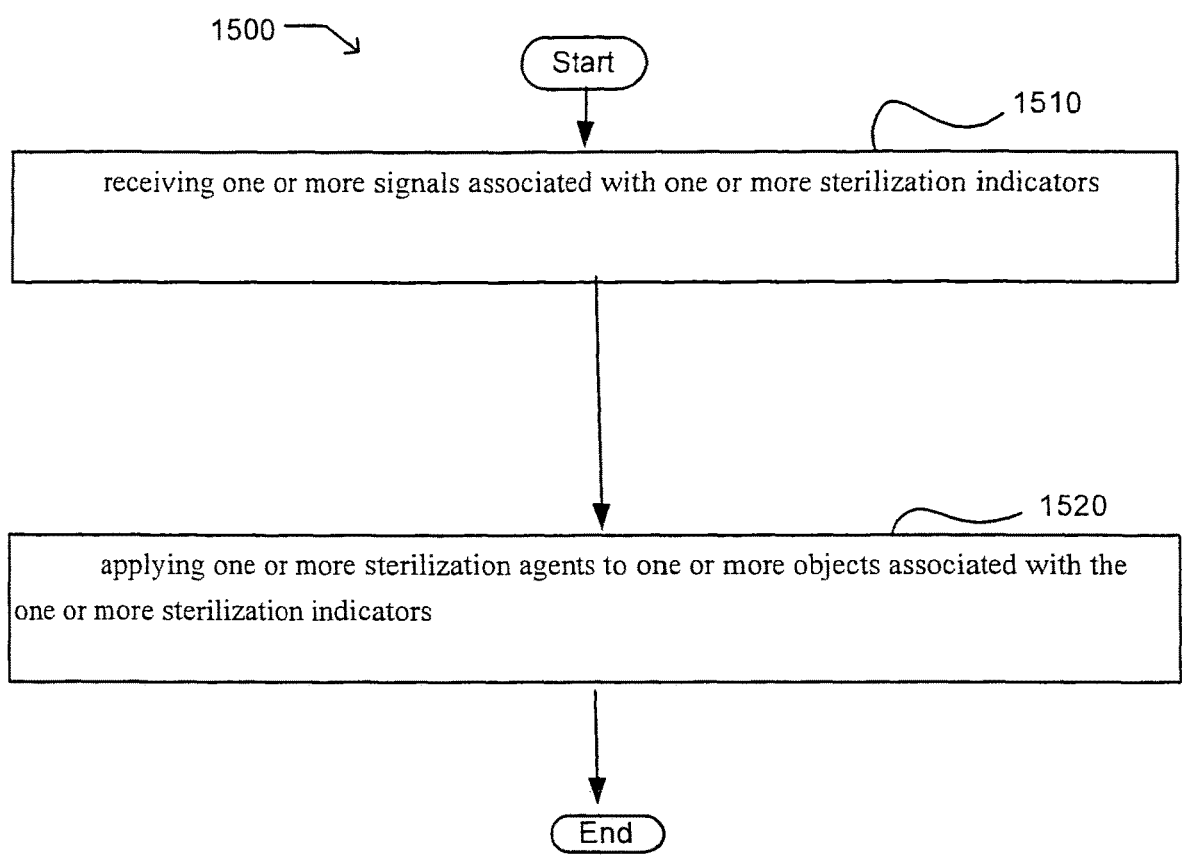
FIG. 15 illustrates an operational flow representing example operations related to sterilization methods.

FIG. 15 illustrates an operational flow 1500 representing examples of operations that are related to the performance of a sterilization method. FIG. 15 illustrates various examples of operations used during performance of the sterilization method, discussion and explanation may be provided with respect to the above-described example of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 1500 includes a receiving operation 1510 involving receiving one or more signals associated with one or more sterilization indicators. In some embodiments, one or more sterilization units 102 may receive one or more signals 110 associated with one or more parameters associated with application of one or more sterilization agents 104 to one or more objects 106. In some embodiments, one or more sterilization units 102 may receive one or more signals 110 associated with one or more times of application, one or more intensities of application, one or more frequencies of application, one or more durations of application, one or more types of sterilization agent used for application, one or more protocols used for application, and/or substantially any combination thereof that is to be used to sterilize one or more objects 106.

The operational flow 1500 also includes an applying operation 1520 involving applying one or more sterilization agents to one or more objects associated with the one or more sterilization indicators. In some embodiments, one or more sterilization units 102 may sense one or more sterilization indicators 108 that are associated with one or more objects 106. In some embodiments, one or more sterilization units 102 may sense the presence of one or more sterilization indicators 108 that are associated with one or more objects 106. In some embodiments, one or more sterilization units 102 may sense the absence of one or more sterilization indicators 108 that are associated with one or more objects 106. In some embodiments, one or more sterilization units 102 may determine what type or types of sterilization agents 104 to apply to one or more objects 106. In some embodiments, one or more sterilization units 102 may determine what type or types of sterilization agents 104 not to apply to one or more objects 106. In some embodiments, one or more sterilization units 102 may determine whether to apply one or more sterilization agents 104 to one or more objects 106 in accordance with a sterilization protocol. In some embodiments, one or more sterilization units 102 may determine the intensity with which to apply one or more sterilization agents 104 to one or more objects 106. In some embodiments, one or more sterilization units 102 may determine the frequency with which to apply one or more sterilization agents 104 to one or more objects 106. In some embodiments, one or more sterilization units 102 may determine when one or more sterilization agents 104 were last applied to one or more objects 106. In some embodiments, one or more sterilization units 102 may determine when one or more sterilization agents 104 should be applied to one or more objects 106.

In some embodiments, one or more sterilization units 102 apply one or more sterilization agents 104 that are selected from the group consisting of light, one or more chemicals and radiation. In some embodiments, one or more sterilization units 102 may apply one or more sterilization agents 104 that include light. In some embodiments, one or more sterilization units 102 apply sterilizing light. In some embodiments, one or more sterilization units 102 may apply ultraviolet light. In some embodiments, one or more sterilization units 102 may apply nonsterilizing light. For example, in some embodiments, visible light may be applied to one or more objects 106. In some embodiments, one or more sterilization units 102 apply one or more sterilization agents 104 that include one or more chemicals. Numerous types of chemicals may be applied by one or more sterilization units 102. In some embodiments, one or more chemicals may be applied that do not sterilize one or more objects 106. For example, in some embodiments, one or more chemicals that are sterilization indicators 108 may be applied to one or more objects 106. In some embodiments, one or more chemicals may be applied to one or more objects 106 that wash the one or more objects 106 without sterilizing the one or more objects 106. In some embodiments, one or more chemicals may be applied that sterilize one or more objects 106. Examples of such chemicals include, but are not limited to, alcohol, chlorine, ammonia, ozone, ethylene oxide, peroxides, acids, bases, and the like. In some embodiments, one or more sterilization units 102 apply one or more sterilization agents 104 that include one or more types of radiation. Examples of types of radiation include, but are not limited to, gamma radiation, infrared radiation, beta radiation, and the like. In some embodiments, one or more sterilization units 102 may apply one type of sterilization agent to one or more objects 106. In some embodiments, one or more sterilization units 102 may apply one or more types of sterilization agents 104 to one or more objects 106.

In some embodiments, one or more sterilization units 102 may apply one or more sterilization agents 104 to one or more humans. In some embodiments, one or more sterilization units 102 may apply one or more sterilization agents 104 to all accessible surfaces of one or more humans. For example, in some embodiments, one or more sterilization units 102 may be configured as a shower where one or more sterilization agents 104 may be applied to one or more humans. In some embodiments, the one or more humans may be covered with clothing or other protective wear. In some embodiments, the one or more humans may not be covered with clothing or other protective wear. In some embodiments, one or more sterilization units 102 may apply one or more sterilization agents 104 to one or more portions of a human. For example, in some embodiments, one or more sterilization units 102 are configured to apply one or more sterilization agents 104 to one or more feet. In some embodiments, one or more sterilization units 102 are configured to apply one or more sterilization agents 104 to one or more hands. In some embodiments, one or more sterilization units 102 are configured to apply one or more sterilization agents 104 to one or more arms and hands. In some embodiments, the one or more portions of one or more humans may be covered with clothing or other protective wear. In some embodiments, the one or more portions of one or more humans may not be covered with clothing or other protective wear.

In some embodiments, one or more sterilization units 102 may apply one or more sterilization agents 104 to one or more hands that are covered with one or more gloves. In some embodiments, one or more sterilization units 102 are configured as hand sterilizers to apply one or more sterilization agents 104 onto one or more hands. In some embodiments, one or more sterilization units 102 are configured to apply one or more gloves to one or more hands. For example, in some embodiments, one or more hands may be placed within one or more sterilization units 102 where gloves may be applied to the one or more hands by the one or more sterilization units 102. In some embodiments, rubber gloves may be stretched over one or more hands that are placed within one or more sterilization units 102. In other embodiments, one or more gloves may be formed on one or more hands through application of one or more coat forming compounds to the one or more hands. For example, in some embodiments, non-toxic paint may be sprayed onto one or more hands to form one or more gloves. In some embodiments, one or more coat forming compounds may be applied to one or more hands that are covered with gloves. For example, one or more hands may each be covered with a latex glove to which one or more coat forming compounds are applied. In some embodiments, metalized gloves are used to cover one or more hands. Numerous examples of metalized gloves are known and are commercially available (i.e., Newtex Industries, Inc., Victor, N.Y.). In some embodiments, one or more hands may be covered with one or more gloves that protect the one or more hands from one or more sterilization agents 104 that are applied to the one or more hands.

In some embodiments, one or more sterilization units 102 may apply one or more sterilization agents 104 to one or more hands that are covered with one or more indicator gloves. In some embodiments, one or more indicator gloves indicate if one or more sterilization agents 104 were applied to the one or more indicator gloves. In some embodiments, one or more indicator gloves indicate when one or more sterilization agents 104 were applied to the one or more indicator gloves. In some embodiments, one or more indicator gloves indicate what type or types of sterilization agents 104 were applied to the one or more indicator gloves. In some embodiments, one or more indicator gloves indicate if one or more sterilization agents 104 should be applied to the one or more indicator gloves. Numerous technologies may be used to produce indicator gloves. In some embodiments, a phosphorescent dye may be included within the indicator gloves that will emit light upon being exposed to ultraviolet light. Accordingly, in some embodiments, such indicator gloves may be used to indicate the intensity with which the indicator gloves were irradiated with ultraviolet light. In some embodiments, such indicator gloves may be used to indicate when the indicator gloves were last irradiated with ultraviolet light. In some embodiments, indicator gloves may include one or more chemicals that change color upon being sterilized. Such chemicals are known and are commercially available (i.e., JP Laboratories, Inc., Middlesex, N.J.). In some embodiments, one or more indicator gloves may include one or more sterilization indicators 108.

In some embodiments, one or more sterilization units 102 may apply one or more sterilization agents 104 to one or more objects 106 according to one or more protocols. In some embodiments, one or more sterilization protocols may be associated with one or more objects 106. In some embodiments, a sterilization protocol may specify the immediacy, latency, intensity and time-integrated intensity of sterilizing radiation that is to be applied to one or more objects 106. In some embodiments, a sterilization protocol may specify one or more types of sterilization agents 104 that are to be applied to one or more objects 106. In some embodiments, a sterilization protocol may specify one or more types of sterilization agents 104 that are not to be applied to one or more objects 106. In some embodiments, a sterilization protocol may specify the frequency with which one or more sterilization agents 104 are to be applied to one or more objects 106. In some embodiments, a sterilization protocol may specify the intensity and/or concentration that one or more types of sterilization agents 104 that are to be applied to one or more objects 106. Numerous sterilization protocols can be assigned to one or more objects 106. In some embodiments, such protocols can be used to specify the intensity with which one or more objects 106 are sterilized to account for high patient-hazard and/or high infectivity use of the one or more objects 106 to ensure that such objects 106 receive rigorous and/or frequent sterilization treatment. Accordingly, in some embodiments, one or more sterilization indicators 108 can communicate with one or more sterilization units 102 to determine if one or more objects 106 have been sterilized in accordance with a sterilization protocol. In some embodiments, one or more sterilization indicators 108 can indicate how much time has passed since one or more objects 106 were last sterilized. In some embodiments, one or more sterilization indicators 108 can communicate with one or more sterilization units 102 to indicate when one or more objects 106 were last sterilized. In other embodiments, one or more sterilization indicators 108 can emit phosphorescent light from one or more phosphorescent materials included within one or more objects 106 to indicate when the one or more objects 106 were last sterilized. In some embodiments, one or more sterilization indicators 108 can communicate with one or more recording units 112 to indicate when one or more objects 106 were last sterilized. In some embodiments, one or more sterilization indicators 108 can communicate with one or more sterilization units 102 to determine when one or more objects 106 were last sterilized.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g. "a" and/or "an" should typically be interpreted to mean ", at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various embodiments described herein can be implemented, individually and/or collectively, by various types of electromechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electromechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electromechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, hovercraft, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g. a networked system, a telephone system, a voice-over IP system, etc.), (f) a business entity (e.g., an Internet Service Provider (ISP) entity such as Comcast Cable, Quest, Southwestern Bell, etc), or (g) a wired/wireless services entity such as Sprint, Cingular, Nextel, etc.), etc.

Although user 118 is shown/described herein as a single illustrated figure, those skilled in the art will appreciate that user 118 may be representative of a human user, a robotic user (e.g., computational entity), and/or substantially any combination thereof (e.g., a user may be assisted by one or more robotic agents). In addition, user 118, as set forth herein, although shown as a single entity may in fact be composed of two or more entities. Those skilled in the art will appreciate that, in general, the same may be said of "sender" and/or other entity-oriented terms as such terms are used herein.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

All publications, patents and patent applications cited herein are incorporated herein by reference. The foregoing specification has been described in relation to certain embodiments thereof, and many details have been set forth for purposes of illustration, however, it will be apparent to those skilled in the art that the invention is susceptible to additional embodiments and that certain of the details described herein may be varied considerably without departing from the basic principles of the invention.

What is claimed is:

1. A system comprising:
   at least one sterilization unit at least one of mountable on at least one wall or configured for positioning on at least one mobile platform in at least one facility, the at least one sterilization unit configured for applying one or more sterilization agents to one or more objects in the at least one facility and including one or more electronic circuitry devices including at least:
   circuitry configured for receiving, via at least one wireless communication link, at least one or more instructions specifying the one or more objects for applying the one or more sterilization agents and specifying one or more sterilization parameters associated with application of the one or more sterilization agents to the specified one or more objects;
   circuitry configured for applying the one or more sterilization agents to the specified one or more objects in accordance with the specified one or more sterilization parameters including at least circuitry configured for steering at least one radiation beam in accordance with at least one sterilization parameter that specifies at least one type of sterilizing radiation for application to the specified one or more objects and at least one sterilization parameter that steers the at least one radiation beam to the specified one or more objects; and
   circuitry configured for transmitting to one or more sterilization indicators associated with the specified one or more objects at least one or more signals indicative of applying the one or more sterilization agents to the specified one or more objects, wherein the transmitting is via the at least one wireless communication link and the at least one or more signals are configured at least for determining whether the specified one or more objects have been sterilized in accordance with one or more sterilization protocols.

2. The system of claim 1, wherein the circuitry configured for applying the one or more sterilization agents to the specified one or more objects in accordance with the specified one or more sterilization parameters comprises:
   at least one of:
      circuitry configured for applying the one or more sterilization agents including at least one or more chemicals;
      circuitry configured for applying the one or more sterilization agents including at least infrared radiation;
      circuitry configured for applying the one or more sterilization agents including at least sonic radiation; or
      circuitry configured for applying the one or more sterilization agents including at least gamma radiation.

3. The system of claim 1, further comprising:
   circuitry configured for transmitting one or more signals indicating at least one determination of whether the specified one or more objects have been sterilized in accordance with the one or more sterilization protocols including at least one of:
      circuitry configured for transmitting the one or more signals to one or more controlling units; or
      circuitry configured for transmitting the one or more signals to one or more recording units.

4. The system of claim 1, wherein the circuitry configured for applying the one or more sterilization agents to the specified one or more objects in accordance with the specified one or more sterilization parameters comprises:
   circuitry configured for applying the one or more sterilization agents including at least ultraviolet light.

5. The system of claim 1, wherein the circuitry configured for transmitting to one or more sterilization indicators associated with the specified one or more objects at least one or more signals indicative of applying the specified one or more sterilization agents to the specified one or more objects comprises:
   circuitry configured for transmitting to one or more sterilization indicators associated with the specified one or more objects at least one or more signals indicative of applying the specified one or more sterilization agents to the specified one or more objects, wherein the transmitting is via the at least one wireless communication link and the one or more signals are configured for reconfiguring the one or more sterilization indicators associated with the specified one or more objects including at least reconfiguring to indicate application of the at least one type of sterilizing radiation to the specified one or more objects.

6. The system of claim 1, wherein the circuitry configured for transmitting to one or more sterilization indicators associated with the specified one or more objects at least one or more signals indicative of applying the specified one or more sterilization agents to the specified one or more objects comprises:
circuitry configured for transmitting to one or more sterilization indicators associated with the specified one or more objects at least one or more signals indicative of applying the specified one or more sterilization agents to the specified one or more objects, wherein the transmitting is via the at least one wireless communication link and the one or more signals are configured for reconfiguring the one or more sterilization indicators associated with the specified one or more objects including at least reconfiguring to indicate one or more parameters associated with application of the at least one type of sterilizing radiation to the specified one or more objects.

7. The system of claim 1, wherein the circuitry configured for applying the one or more sterilization agents to the specified one or more objects in accordance with the specified one or more sterilization parameters comprises:
circuitry configured for applying the one or more sterilization agents to the specified one or more objects in accordance with the specified one or more sterilization parameters specified by the at least one or more instructions wherein the specified one or more objects are associated with the one or more sterilization indicators included in one or more gloves that indicate at least an intensity of application of the one or more sterilization agents.

8. The system of claim 7, wherein the circuitry configured for applying the one or more sterilization agents to the specified one or more objects in accordance with the specified one or more sterilization parameters comprises:
circuitry configured for applying the one or more sterilization agents to the specified one or more objects in accordance with the specified one or more sterilization parameters specified by the at least one or more instructions wherein the specified one or more objects are associated with the one or more sterilization indicators that indicate at least application of one or more types of the one or more sterilization agents.

9. The system of claim 1, wherein the circuitry configured for applying the one or more sterilization agents to the specified one or more objects in accordance with the specified one or more sterilization parameters comprises:
circuitry configured for receiving one or more optical signals indicating at least an intensity of application of the one or more sterilization agents.

10. The system of claim 1, wherein the circuitry configured for applying the one or more sterilization agents to the specified one or more objects in accordance with the specified one or more sterilization parameters comprises:
circuitry configured for applying the one or more sterilization agents to the specified one or more objects in accordance with the specified one or more sterilization parameters including at least circuitry configured for shaping at least one radiation beam in accordance with at least one sterilization parameter that shapes the at least one radiation beam for application of the shaped at least one radiation beam to the specified one or more objects.

11. The system of claim 1, wherein the circuitry configured for applying the one or more sterilization agents to the specified one or more objects in accordance with the specified one or more sterilization parameters comprises:
circuitry configured for applying the one or more sterilization agents to the specified one or more objects in accordance with the specified one or more sterilization parameters including at least circuitry configured for shaping and steering at least one radiation beam in accordance with at least one sterilization parameter that shapes and steers the at least one radiation beam to the specified one or more objects for application of the shaped and steered at least one radiation beam to the specified one or more objects.

12. The system of claim 1, wherein the circuitry configured for applying the one or more sterilization agents to the specified one or more objects in accordance with the specified one or more sterilization parameters comprises:
at least one of:
circuitry configured for applying the one or more sterilization agents to the specified one or more objects in accordance with at least one sterilization parameter that specifies at least one type of sterilizing radiation for not applying the one or more sterilization agents to the specified one or more objects; or
circuitry configured for applying the one or more sterilization agents to the specified one or more objects in accordance with at least one sterilization parameter that specifies whether to apply the one or more sterilization agents to the specified one or more objects.

13. The system of claim 1, wherein the circuitry configured for applying the one or more sterilization agents to the specified one or more objects in accordance with the specified one or more sterilization parameters comprises:
at least one of:
circuitry configured for applying the one or more sterilization agents to the specified one or more objects in accordance with at least one sterilization parameter that specifies at least one intensity for applying the one or more sterilization agents to the specified one or more objects; or
circuitry configured for applying the one or more sterilization agents to the specified one or more objects in accordance with at least one sterilization parameter that specifies at least one frequency for applying the one or more sterilization agents to the specified one or more objects.

14. The system of claim 1, wherein the circuitry configured for applying the one or more sterilization agents to the specified one or more objects in accordance with the specified one or more sterilization parameters comprises:
circuitry configured for applying the one or more sterilization agents to the specified one or more objects in accordance with at least one sterilization parameter that specifies when one or more sterilization agents were last applied to the specified one or more objects.

15. The system of claim 1, wherein the circuitry configured for applying the one or more sterilization agents to the specified one or more objects in accordance with the specified one or more sterilization parameters comprises:
circuitry configured for applying multiple types of chemical sterilization agents to the specified one or more objects in accordance with the specified one or more sterilization parameters specified by the at least one or more instructions.

16. The system of claim 1, wherein the circuitry configured for applying the one or more sterilization agents to the specified one or more objects in accordance with the specified one or more sterilization parameters comprises:
  circuitry configured for applying multiple types of radiation sterilization agents to the specified one or more objects in accordance with the specified one or more sterilization parameters specified by the at least one or more instructions.

17. The system of claim 1, wherein the circuitry configured for applying the one or more sterilization agents to the specified one or more objects in accordance with the specified one or more sterilization parameters comprises:
  circuitry configured for applying multiple types of radiation sterilization agents to the specified one or more objects in accordance with the specified one or more sterilization parameters specified by the at least one or more instructions including one or more parameters indicative of one or more of immediacy, latency, intensity, or time-integrated intensity of sterilizing radiation of the multiple types of radiation sterilization agents associated with the specified one or more objects.

18. The system of claim 1, wherein the circuitry configured for applying the one or more sterilization agents to the specified one or more objects in accordance with the specified one or more sterilization parameters comprises:
  circuitry configured for applying multiple types of radiation sterilization agents to the specified one or more objects in accordance with the specified one or more sterilization parameters specified by the at least one or more instructions designating one or more of type, frequency, or duration for applying the multiple types of radiation sterilization agents to the specified one or more objects.

19. The system of claim 1, further comprising:
  the one or more sterilization indicators configured for indicating at least an intensity at which the one or more sterilization agents have been applied to the specified one or more objects.

20. The system of claim 1, further comprising:
  at least one of:
    the one or more sterilization indicators configured for indicating at least one or more types of the one or more sterilization agents have been applied to the specified one or more objects; or
    the one or more sterilization indicators configured for indicating whether the one or more sterilization agents should be applied to the specified one or more objects.

* * * * *